(12) United States Patent
Tamura et al.

(10) Patent No.: US 10,066,060 B2
(45) Date of Patent: Sep. 4, 2018

(54) PRODUCTION METHOD FOR HIGH-PURITY ORGANOSILICON COMPOUND

(71) Applicant: Dow Corning Toray Co., Ltd., Tokyo (JP)

(72) Inventors: Seiki Tamura, Ichihara (JP); Tatsuo Souda, Ichihara (JP); Sayuri Sawayama, Ichihara (JP); Seiji Hori, Sabae (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 345 days.

(21) Appl. No.: 14/655,144

(22) PCT Filed: Dec. 26, 2013

(86) PCT No.: PCT/JP2013/085006
§ 371 (c)(1),
(2) Date: Sep. 21, 2015

(87) PCT Pub. No.: WO2014/104257
PCT Pub. Date: Jul. 3, 2014

(65) Prior Publication Data
US 2015/0376346 A1    Dec. 31, 2015

(30) Foreign Application Priority Data
Dec. 28, 2012    (JP) .................. 2012-289016

(51) Int. Cl.
| | |
|---|---|
| C07F 7/04 | (2006.01) |
| C08G 77/46 | (2006.01) |
| C07F 7/20 | (2006.01) |
| C08G 77/34 | (2006.01) |
| C08L 83/12 | (2006.01) |
| A61Q 19/00 | (2006.01) |
| A61K 8/894 | (2006.01) |
| C08G 77/38 | (2006.01) |

(52) U.S. Cl.
CPC .............. *C08G 77/46* (2013.01); *A61K 8/894* (2013.01); *A61Q 19/00* (2013.01); *C07F 7/20* (2013.01); *C08G 77/34* (2013.01); *C08G 77/38* (2013.01); *C08L 83/12* (2013.01); *A61K 2800/10* (2013.01)

(58) Field of Classification Search
CPC ........ C08G 77/46; C08G 77/34; A61K 8/894; A61Q 19/00; C07F 7/20; C08L 83/12
USPC ....................................................... 556/467
See application file for complete search history.

(56) References Cited

U.S. PATENT DOCUMENTS

| | | |
|---|---|---|
| 2,383,521 A | 8/1945 | Sowa |
| 3,867,420 A | 2/1975 | Morehouse et al. |
| 3,957,843 A | 5/1976 | Bennett |
| 4,246,423 A | 1/1981 | Martin |
| 4,431,789 A | 2/1984 | Okazaki et al. |
| 5,032,662 A | 7/1991 | Berger et al. |
| 5,132,392 A | 7/1992 | DeYoung et al. |
| 5,225,509 A | 7/1993 | Heinrich et al. |
| 5,288,831 A | 2/1994 | Ichinohe et al. |
| 5,466,849 A | 11/1995 | Shioya et al. |
| 5,660,819 A | 8/1997 | Tsubaki et al. |
| 5,789,612 A * | 8/1998 | Graiver .................. C08G 77/08 556/450 |
| 5,844,010 A | 12/1998 | Burkhart et al. |
| 5,847,180 A | 12/1998 | Gravier et al. |
| 6,187,891 B1 | 2/2001 | Rautschek et al. |
| 6,649,692 B2 | 11/2003 | Yu et al. |
| 6,784,271 B2 | 8/2004 | Nakanishi |
| 6,987,157 B2 | 1/2006 | Clement et al. |
| 7,153,922 B2 | 12/2006 | Hohberg et al. |
| 7,427,648 B2 | 9/2008 | Ochs et al. |
| 7,655,744 B2 | 2/2010 | Miyanaga |

(Continued)

FOREIGN PATENT DOCUMENTS

| | | |
|---|---|---|
| EP | 0 905 171 A1 | 3/1999 |
| EP | 0 924 238 A1 | 6/1999 |

(Continued)

OTHER PUBLICATIONS

English language abstract for WO 2004/046226 extracted from espacenet.com database on Oct. 12, 2015, 1 page.

(Continued)

*Primary Examiner* — Clinton Brooks
*Assistant Examiner* — Kofi Adzamli
(74) *Attorney, Agent, or Firm* — Howard & Howard Attorneys PLLC

(57) ABSTRACT

The present invention relates to a production method for a liquid high-purity organosilicon compound, the method comprising the steps of:

adding, to a mixture containing an organosilicon compound selected from a group consisting of organomodified silicones and organomodified silanes and impurities, an organic wax having affinity with the impurities and having a higher melting point than the organosilicon compound, melting and mixing while heating, and introducing the impurities into the melted organic wax;

obtaining a solidified product of the organic wax by cooling the organic wax; and performing solid/liquid phase separation on the organosilicon compound and the solidified product of the organic wax.

With the present invention, it is possible to provide a useful method for producing a high-purity organosilicon compound stably and on a commercial scale.

12 Claims, No Drawings

(56) References Cited

U.S. PATENT DOCUMENTS

| | | | |
|---|---|---|---|
| 7,709,671 | B2 | 5/2010 | Nishijima et al. |
| 7,771,709 | B2 | 8/2010 | Nakanishi et al. |
| 7,825,205 | B2 | 11/2010 | Knott et al. |
| 7,825,209 | B2 | 11/2010 | Knott et al. |
| 8,013,097 | B2 | 9/2011 | Kennan et al. |
| 8,076,442 | B2 | 12/2011 | Moeller et al. |
| 8,715,626 | B2 | 5/2014 | Tamura et al. |
| 8,784,787 | B2 | 7/2014 | Tamura et al. |
| 8,828,410 | B2 | 9/2014 | Sakuta |
| 9,133,309 | B2 | 9/2015 | Iimura et al. |
| 2002/0131947 | A1 | 9/2002 | Nakanishi |
| 2003/0158363 | A1 | 8/2003 | Nakanishi |
| 2004/0053810 | A1 | 3/2004 | Tully et al. |
| 2004/0253197 | A1 | 12/2004 | Sakuta |
| 2006/0018935 | A1 | 1/2006 | Nishijima et al. |
| 2012/0269748 | A1 | 10/2012 | Tamura et al. |

FOREIGN PATENT DOCUMENTS

| | | |
|---|---|---|
| EP | 1 424 365 A1 | 6/2004 |
| EP | 0 995 771 B1 | 6/2005 |
| JP | S 51-008440 A | 3/1976 |
| JP | S 51-008440 B | 3/1976 |
| JP | S 56-062824 A | 5/1981 |
| JP | S 62-034039 A | 7/1987 |
| JP | S 62-034039 B | 7/1987 |
| JP | S 62-195389 A | 8/1987 |
| JP | S 63-202629 A | 8/1988 |
| JP | H 01-249109 A | 10/1989 |
| JP | H 02-302438 A | 12/1990 |
| JP | H 04-108795 A | 4/1992 |
| JP | H 04-211605 A | 8/1992 |
| JP | H 04-234307 A | 8/1992 |
| JP | H 05-156019 A | 6/1993 |
| JP | H 05-186596 A | 7/1993 |
| JP | H 05-310944 A | 11/1993 |
| JP | H 06-089147 A | 3/1994 |
| JP | H 06-100676 A | 4/1994 |
| JP | H 07-126392 A | 5/1995 |
| JP | H 07-304627 A | 11/1995 |
| JP | H 07-330907 A | 12/1995 |
| JP | H 08-073596 A | 3/1996 |
| JP | H 08-208426 A | 8/1996 |
| JP | H 09-012723 A | 1/1997 |
| JP | H 09-165315 A | 6/1997 |
| JP | H 09-165318 A | 6/1997 |
| JP | H 09-194594 A | 7/1997 |
| JP | H 10-279807 A | 10/1998 |
| JP | H 11-181096 A | 7/1999 |
| JP | H 11-240951 A | 9/1999 |
| JP | 2000-063523 A | 2/2000 |
| JP | 2000-128992 A | 5/2000 |
| JP | 2002-179798 A | 6/2002 |
| JP | 2003-096192 A | 4/2003 |
| JP | 2004-525205 A | 8/2004 |
| JP | 2004-528412 A | 9/2004 |
| JP | 2004-331977 A | 11/2004 |
| JP | 2004-339244 A | 12/2004 |
| JP | 2005-042097 A | 2/2005 |
| JP | 2005-089494 A | 4/2005 |
| JP | 2005-120293 A | 5/2005 |
| JP | 2005-120937 A | 5/2005 |
| JP | 2005-535760 A | 11/2005 |
| JP | 2005-344116 A | 12/2005 |
| JP | 2008-156637 A | 7/2008 |
| JP | 2008-156638 A | 7/2008 |
| JP | 2008-534721 A | 8/2008 |
| JP | 2010-523790 A | 7/2010 |
| JP | 2012-046507 A | 3/2012 |
| JP | 2012-246445 A | 12/2012 |
| WO | WO 02/055588 A1 | 7/2002 |
| WO | WO 03/020828 A1 | 3/2003 |
| WO | WO 2004/046226 A1 | 6/2004 |
| WO | WO 2008/127519 A1 | 10/2008 |
| WO | WO 2011/049246 A1 | 4/2011 |
| WO | WO 2011/049247 A1 | 4/2011 |
| WO | WO 2011/049248 A1 | 4/2011 |
| WO | WO 2012/165227 A1 | 12/2012 |
| WO | WO 2014/104256 A1 | 7/2014 |

OTHER PUBLICATIONS

English language abstract for WO 2011/049246 extracted from espacenet.com database on Oct. 12, 2015, 2 pages.

English language abstract for WO 2011/049247 extracted from espacenet.com database on Oct. 12, 2015, 2 pages.

English language abstract for WO 2011/049248 extracted from espacenet.com database on Oct. 12, 2015, 2 pages.

English language abstract and machine-assisted English translation for WO 2012/165227 extracted from the PAJ database on Oct. 12, 2015, 90 pages.

English language abstract for WO 2014/104256 extracted from espacenet.com database on Oct. 12, 2015, 1 page.

International Search Report for Application No. PCT/JP2013/085005 dated Apr. 22, 2014, 5 pages.

International Search Report for Application No. PCT/JP2013/085006 dated Apr. 22, 2014, 5 pages.

English language abstract not found for JPS 51-008440; however, see English language equivalent U.S. Pat. No. 3,957,843. Original document extracted from espacenet.com on Oct. 12, 2015, 12 pages.

English language abstract not found for JPS 56-062824; however, see English language equivalent U.S. Pat. No. 4,246,423. Original document extracted from espacenet.com on Oct. 12, 2015, 15 pages.

English language abstract not found for JPS 62-034039; however, see English language equivalent U.S. Pat. No. 4,431,789. Original document extracted from espacenet.com on Oct. 12, 2015, 12 pages.

English language abstract and machine-assisted English translation for JPS 62-195389 extracted from the PAJ database on Jul. 1, 2015, 6 pages.

English language abstract for JPS 63-202629 extracted from the PAJ database on Jul. 1, 2015, 1 page.

English language abstract for JPH 01-249109 extracted from espacenet.com database on Oct. 12, 2015, 2 pages.

English language abstract for JPH 02-302438 extracted from espacenet.com database on Oct. 12, 2015, 1 page.

English language abstract for JPH 04-108795 extracted from espacenet.com database on Oct. 12, 2015, 2 pages.

English language abstract for JPH 04-211605 extracted from espacenet.com database on Oct. 12, 2015, 1 page.

English language abstract for JPH 04-234307 extracted from espacenet.com database on Oct. 12, 2015, 1 page.

English language abstract and machine-assisted English translation for JPH 05-156019 extracted from espacenet.com database on Oct. 12, 2015, 13 pages.

English language abstract and machine-assisted English translation for JPH 05-186596 extracted from espacenet.com database on Oct. 12, 2015, 32 pages.

English language abstract and machine-assisted English translation for JPH 05-310944 extracted from espacenet.com database on Oct. 12, 2015, 13 pages.

English language abstract and machine-assisted English translation for JPH 06-089147 extracted from PAJ database on Oct. 12, 2015, 20 pages.

English language abstract not found for JPH 06-100676; however, see English language equivalent U.S. Pat. No. 5,132,392. Original document extracted from espacenet.com on Oct. 12, 2015, 10 pages.

English language abstract and machine-assisted English translation for JPH 07-126392 extracted from espacenet.com database on Oct. 12, 2015, 12 pages.

English language abstract and machine-assisted English translation for JPH 07-304627 extracted from espacenet.com database on Oct. 12, 2015, 19 pages.

English language abstract and machine-assisted English translation for JPH 07-330907 extracted from espacenet.com database on Oct. 12, 2015, 19 pages.

(56) References Cited

OTHER PUBLICATIONS

English language abstract and machine-assisted English translation for JPH 08-073596 extracted from PAJ database on Jun. 18, 2015, 26 pages.
English language abstract and machine-assisted English translation for JPH 08-208426 extracted from espacenet.com database on Oct. 12, 2015, 21 pages.
English language abstract and machine-assisted English translation for JPH 09-012723 extracted from PAJ database on Jun. 18, 2015, 13 pages.
English language abstract and machine-assisted English translation for JPH 09-165315 extracted from espacenet.com database on Oct. 12, 2015, 23 pages.
English language abstract and machine-assisted English translation for JPH 09-165318 extracted from espacenet.com database on Oct. 12, 2015, 23 pages.
English language abstract and machine-assisted English translation for JPH 09-194594 extracted from espacenet.com database on Oct. 12, 2015, 29 pages.
English language abstract for JPH 10-279807 extracted from espacenet.com database on Oct. 12, 2015, 2 pages.
English language abstract for JPH 11-181096 extracted from espacenet.com database on Oct. 12, 2015, 1 page.
English language abstract for JPH 11-240951 extracted from espacenet.com database on Oct. 12, 2015, 1 page.
English language abstract for JP 2000-063523 extracted from espacenet.com database on Oct. 8, 2015, 2 pages.
English language abstract for JP 2000-128992 extracted from espacenet.com database on Oct. 8, 2015, 1 page.
English language abstract for JP 2002-179798 extracted from espacenet.com database on Oct. 12, 2015, 2 pages.
English language abstract and machine-assisted English translation for JP 2003-096192 extracted from PAJ database on Oct. 12, 2015, 24 pages.
English language abstract not found for JP 2004-525205; however, see English language equivalent U.S. Pat. No. 6,987,157. Original document extracted from espacenet.com on Oct. 12, 2015, 50 pages.
English language abstract not found for JP 2004-528412; however, see English language equivalent U.S. Pat. No. 6,649,692. Original document extracted from espacenet.com on Oct. 8, 2015, 51 pages.
English language abstract for JP 2004-331977 extracted from espacenet.com database on Oct. 8, 2015, 2 pages.
English language abstract for JP 2004-339244 extracted from espacenet.com database on Oct. 12, 2015, 2 pages.
English language abstract for JP 2005-042097 extracted from espacenet.com database on Oct. 12, 2015, 2 pages.
English language abstract and machine-assisted English translation for JP 2005-089494 extracted from espacenet.com database on Oct. 12, 2015, 31 pages.
English language abstract and machine-assisted English translation for JP 2005-120937 extracted from espacenet.com database on Oct. 12, 2015, 29 pages.
English language abstract not found for JP 2005-535760; however, see English language equivalent U.S. 2004/0053810. Original document extracted from espacenet.com on Oct. 12, 2015, 32 pages.
English language abstract for JP 2005-344116 extracted from espacenet.com database on Oct. 12, 2015, 1 page.
English language abstract for JP 2008-156637 extracted from espacenet.com database on Oct. 12, 2015, 1 page.
English language abstract for JP 2008-156638 extracted from espacenet.com database on Oct. 12, 2015, 1 page.
English language abstract not found for JP 2008-534721; however, see English language equivalent U.S. Pat. No. 8,076,442. Original document extracted from espacenet.com on Oct. 12, 2015, 48 pages.
English language abstract not found for JP 2010-523790; however, see English language equivalent U.S. Pat. No. 8,013,097. Original document extracted from espacenet.com on Oct. 12, 2015, 8 pages.
English language abstract for JP 2012-046507 extracted from espacenet.com database on Oct. 12, 2015, 1 page.
English language abstract and machine-assisted English translation for JP 2012-246445 extracted from PAJ database on Oct. 12, 2015, 91 pages.
English language abstract for WO 02/055588 extracted from espacenet.com database on Oct. 12, 2015, 2 page.
English language abstract for WO 03/020828 extracted from espacenet.com database on Oct. 12, 2015, 1 page.
English language abstract and machine-assisted English translation for JP 2005-120293 extracted from the PAJ database on Oct. 26, 2015, 50 pages.
English language abstract not found for JP 2010-523790; however, see English language equivalent U.S. Pat. No. 8,013,097. Original document extracted from espacenet.com on Oct. 12, 2015, 8 pages. (JP 2010-523790 was previously submitted but was incomplete—see attached full text of JP 2010-523790).

\* cited by examiner

PRODUCTION METHOD FOR HIGH-PURITY ORGANOSILICON COMPOUND

RELATED APPLICATIONS

This application is the National Stage of International Patent Application No. PCT/JP2013/085006, filed on Dec. 26, 2013, which claims priority to and all the advantages of Japanese Patent Application No. 2012-289016, filed on Dec. 28, 2012, the content of which is incorporated herein by reference.

TECHNICAL FIELD

The present invention relates to a production method for a high-purity organosilicon compound. Further, the present invention relates to the use of the aforementioned high-purity organosilicon compound in external preparations, cosmetics, and various industrial materials.

Organosilicon compounds are broadly classified into organomodified silanes, which are a group of compounds with a relatively low molecular weight in which the number of silicon atoms contained in each molecule is from 1 to several atoms, and silicones, which are polymers in which the number of silicon atoms contained in each molecule is 2 or more atoms and which are typically classified as polymer compounds. In addition, silicones can be classified into silicone oils, silicone resins, silicone elastomers, silicone rubbers, and the like in accordance with the characteristics or structure thereof.

BACKGROUND ART

Organomodified silicones have been produced by conventionally known reaction schemes in accordance with the types of organic groups introduced into the silicone. Since there are typically few cases in which the reaction for introducing organic groups progresses at a chemical equivalent (molar equivalent) level, the introduction reaction is ordinarily completed by using an excessive amount of an organic modifier. Accordingly, the unreacted organic modifier is present in the reaction system in addition to the organomodified silicone serving as a product.

When the organic modifier is a compound with a relatively low boiling point such as an α-olefin having at most 12 carbon atoms, the residual compound (impurities) can be reduced by stripping treatment, whereby the reaction mixture is heated so as to establish a decompressed state. However, when the boiling point of the organic modifier is high, or when the organic modifier is a polymer compound, purification by means of stripping is not effective, so it has been difficult to obtain a high-purity organomodified silicone on a commercial scale. This is due to not only the fact that stripping at an excessively high temperature causes the degeneration of the product or undesirable side reactions, but also the fact that a technique of stripping impurities having a high boiling point at an even higher temperature is inefficient in an actual production process.

Another technique for increasing the purity of an organomodified silicone containing a residual organic modifier is an extraction (or precipitation/re-precipitation) separation method utilizing the difference in solubility between impurities and the main component. For example, when the organic modifier is a hydrophilic compound, in an extraction separation method, most impurities are first extracted and removed with a hydrophilic solvent (alternatively, the main component is conversely extracted with a lipophilic solvent). However, phase separation in the extraction process ordinarily takes time, and this does not yield clean separation. This results in an increase in waste and a decrease in yield and productivity. In addition, depending on the structure of the organomodified silicone, there are many cases in which the entire system enters an emulsified state and cannot be separated, which leads to poor versatility.

On the other hand, a precipitation and re-precipitation method is a technique of dissolving an organomodified silicone containing a residual organic modifier in an organic solvent with solubility in both the impurities and the main component, and precipitating and separating the main component by gradually adding water, for example. Patent Document 1 discloses a high-purity polypropylene glycol-modified organosiloxane polymer obtained by a precipitation and re-precipitation method. However, the total amounts of the organic solvent and water that are used in this method are ten times the amount of the organomodified silicone each time re-precipitation is performed, and this is repeated three times to obtain a high-purity organomodified silicone with no impurities. Accordingly, taking into consideration problems such as the low productivity in relation to the number of reactions and the large amount of waste water treatment, application to mass production on a commercial scale is difficult. In addition, when the organic modifier is a polyethylene glycol (PEG) type modifier, the hydrophilicity and surface activity performance of the corresponding organomodified silicone are increased, so separation and purification are often difficult with this method.

Patent Document 2 discloses an organopolysiloxane derivative having a sugar residue but not containing an unreacted starting material, which is obtained by a membrane separation method using a dialysis tube. However, a dialysis time of three days is required to obtain 10 g of a high-purity organomodified silicone, so this method cannot be considered suitable for mass production on a commercial scale from the perspective of efficiency. In addition, in Patent Document 2, it is stated that the purification of the organopolysiloxane derivative is also possible by column chromatography. Further, Patent Document 3 discloses a glyceryl ether-modified silicone purified by a silica gel column. However, column chromatography requires the circulation of a large amount of a solvent in order to obtain a high-purity organomodified silicone, and there are many problems with production on a commercial scale, such as the apparatus design, the recovery of the waste solvent, the removal of the solvent from the recovered solution, and low productivity.

Another example of a technique for increasing the purity of an organomodified silicone containing a residual organic modifier is an attempt to improve the transparency of a product by repeating precision filtration or adsorption agent treatment so as to reduce the amount of the residual organic modifier, which is also a cause of turbidity or phase separation. However, this residual organic modifier is ordinarily a liquid in the temperature range in which the organomodified silicone serving as the main component is in the liquid phase, so a technique of solid/liquid separation utilizing a filter aid, a cartridge filter, or the like is not only irrational, but is also mostly ineffective in actuality.

Patent Document 4 discloses a purification method for an alkyl glyceryl polysiloxane derivative by means of ultrafiltration utilizing a diafiltration method. However, since the pore diameter of an ultrafiltration membrane is small and the film tends to become obstructed in a short amount of time, ultrafiltration must be performed after diluting an organomodified silicone containing an organic modifier around ten times with a volatile solvent such as hexane. Therefore, there are problems such as the removal of the solvent from the filtrate, low productivity, and operator safety.

In addition, the techniques of Patent Documents 5 to 12 are known as purification methods for polyether-modified silicone compositions. Polyether-modified silicones are typically produced by performing an addition reaction on an organohydrogensiloxane and a polyoxyalkylene having a terminal double bond in the presence of a precious metal catalyst such as chloroplatinic acid. Patent Documents 5 to 12 disclose deodorization techniques of stabilizing the unsaturated group portion of excess polyether (residual organic modifier), which is a cause of the odorization of the polyether-modified silicone composition, by means of hydrolysis or hydrogenation treatment, and it is not the case that a high-purity polyether-modified silicone is obtained. In these techniques, the excess polyether changes the structure thereof and continues to remain in the composition.

On the other hand, there have also been reported attempts to produce a high-purity polyether-modified silicone from the synthesis stage rather than purifying a polyether-modified silicone composition by means of after-treatment. A representative technique is one in which an organic modifier with a structure that is unlikely to cause isomerization, such as γ,γ-dimethylallyl etherified polyoxyalkylene, is used as a polyether starting material instead of a conventional allyl etherified polyoxyalkylene (Patent Documents 13 to 16). However, the unsaturated alcohol used as an initiator in order to obtain this polyether starting material is not a substance that can be obtained easily, so this is not a method with which the polyether-modified silicone can be mass-produced inexpensively. In addition, this unsaturated alcohol serving as an initiator is a tertiary alcohol, and the addition reactivity of alkylene oxide to this alcohol is much worse than when a conventional allyl alcohol (primary alcohol) is used. Therefore, with an ordinary catalyst, there are problems such as residual initiator alcohol with low reactivity, difficulty in obtaining a polyether starting material with the desired degree of polymerization, and a broad molecular weight distribution. In addition, ether bonds adjacent to quaternary carbons of γ,γ-dimethylallyl etherified polyoxyalkylene are unstable and are susceptible to hydrolysis, so at the time of the production of a polyether-modified silicone, it is necessary to use a slightly excessive amount of organohydrogensiloxane and to be careful that the entire amount of the polyoxyalkylene is consumed and not left behind. If left behind in even a slight amount, there is a risk that a strong odor will be generated due to degradation products of low molecular weight after the polyether-modified silicone is blended into a cosmetic or the like, so it is difficult to stabilized production activities or quality from the perspective of the formulation design or confirmation operation for complete consumption.

In addition, similar techniques have been reported in which a long-chain alkenyl etherified polyoxyalkylene (Patent Document 17) or a vinyl etherified polyoxyalkylene (Patent Document 18) is used instead of a conventional allyl etherified polyoxyalkylene. However, a long-chain alkenyl etherified polyoxyalkylene is isomerized during a hydrosilylation reaction, so approximately 10 wt. % remains in the reaction product. Therefore, a high-purity polyether-modified silicone cannot be obtained with the technique of Patent Document 17. On the other hand, although a vinyl etherified polyoxyalkylene is unlikely to cause isomerization, according to Patent Document 18, when Si—H groups and vinyl groups are reacted so as to be equimolar, the reaction is not completed, and Si—H groups remain in an amount of from 5 to 80 ppm. This means that unreacted vinyl etherified polyoxyalkylene is left behind, so a high-purity polyether-modified silicone cannot be obtained with this method either. In addition, vinyl ether-type compounds always have various problems in that the vinyl groups tend to react with hydroxyl groups in the reaction mixture and form acetal, which makes the compound susceptible to vinyl-type polymerization.

Another technique attempting to produce a high-purity polyether-modified silicone from the synthesis stage is reported in Patent Document 19. This consists of a process of performing a hydrosilylation reaction on an alcohol compound containing carbon-carbon double bonds with a relatively low molecular weight and an organohydrogensiloxane, removing the unreacted starting material or the like by stripping so as to obtain a high-purity alcohol-modified polysiloxane, and then addition-polymerizing alkylene oxide with this product. However, in this method, Lewis acid is used a catalyst for addition polymerization, so the coloration of the resulting polyether-modified silicone is strong, and it is also difficult to remove the catalyst. In addition, cyclic polyether impurities resulting from the homopolymerization of alkylene oxide are likely to be produced, and it is difficult to obtain a high-purity polyether-modified silicone with good reproducibility. Further, the process is too complex and unrealistic for silicone producers.

As described above, when the boiling point of the organic modifier is high or when the organic modifier is a polymer compound, there have been practically no known useful methods for stably producing a high-purity organomodified silicone on a commercial scale. Further, there has also been no known technique of increasing the purity of an organomodified silicone which can be applied regardless of the type of organic modifier and can reasonably accommodate production on a commercial scale.

On the other hand, organomodified silanes are typically sold after the purity is increased by distillation purification, even in industrial production, due to the property of being low-molecular compounds having a boiling point. In the production of organomodified silanes, the purity is wholly increased by distillation after being partially purified by extraction or the like following a synthesis reaction due to the fact that plants are already provided with precision distillation equipment and the fact that they are monomolecular so, in contrast to organomodified silicones, problems such as sub-reactions or gelification are unlikely to occur even when distillation is performed at a high temperature. That is, organomodified silanes often have a high boiling point, and the production process causes increases in energy cost when performed at a high temperature for a long period of time, but it is accepted that this is inevitably translated into the sales price. Therefore, there has been practically no search for techniques for increasing purity as an alternative to distillation.

In particular, when the organic modifier of an organomodified silane is a polymer compound such as a polyether or a compound with a high boiling point so that distillation is difficult, purification by distillation is not possible, so it has been difficult to obtain high-purity organomodified silanes.

PRIOR ART DOCUMENT

Patent Document

Patent Document 1: Japanese Unexamined Patent Application Publication No. S63-202629A
Patent Document 2: Japanese Patent No. 3172787 (Japanese Unexamined Patent Application Publication No. H05-186596)
Patent Document 3: Japanese Patent No. 2613124 (Japanese Unexamined Patent Application Publication No. H-04-188795)
Patent Document 4: Japanese Unexamined Patent Application Publication No. H05-156019A
Patent Document 5: Japanese Unexamined Patent Application Publication No. H2-302438 (Japanese Examined Patent Application Publication No. H07-091389)
Patent Document 6: U.S. Pat. No. 5,225,509
Patent Document 7: Japanese Unexamined Patent Application Publication No. H7-330907A
Patent Document 8: Japanese Unexamined Patent Application Publication No. H9-165315A
Patent Document 9: Japanese Unexamined Patent Application Publication No. H9-165318A
Patent Document 10: WO/2002/055588
Patent Document 11: WO/2004/046226
Patent Document 12: Japanese Unexamined Patent Application Publication No. 2005-1202937
Patent Document 13: U.S. Patent No. 3957843 (Japanese Examined Patent Application Publication No. S51-008440)
Patent Document 14: Japanese Unexamined Patent Application Publication No. H8-208426A
Patent Document 15: Japanese Unexamined Patent Application Publication No. H9-012723A
Patent Document 16: U.S. Patent No. 6987157 (Japanese Unexamined Patent Application Publication (Translation of PCT Application No. 2004-525205)
Patent Document 17: Japanese Patent No. 3084200 (Japanese Unexamined Patent Application Publication No. H07-304627)
Patent Document 18: Japanese Patent No. 0995771 (Japanese Unexamined Patent Application Publication No. 2000-128992)
Patent Document 19: Japanese Patent No.4906203 (Japanese Unexamined Patent Application Publication No. 2003-096192)
Patent Document 20: WO/2011/049248
Patent Document 21: WO/2011/049247
Patent Document 22: WO/2011/049246
Patent Document 23: Japanese Unexamined Patent Application Publication No. 2012-046507

SUMMARY OF INVENTION

Technical Problem

The present invention was conceived in light of the problems described above, and an object thereof is to provide a technique for increasing the purity of an organosilicon compound which can be applied regardless of the type of the organic modifier and can reasonably accommodate production on a commercial scale.

In particular, an object of the present invention is to provide a method for stably producing a high-purity organosilicon compound on a commercial scale, even when the boiling point of the organic modifier is high or the organic modifier is a polymer compound.

In addition, another object of the present invention is to use a high-purity organosilicon compound produced with such a method in external preparations, cosmetics, or various industrial materials.

Solution to Problem

The object of the present invention can be achieved by a production method for a liquid high-purity organosilicon compound, the method comprising the steps of:
adding, to a mixture containing an organosilicon compound selected from a group consisting of organomodified silicones and organomodified silanes and impurities, an organic wax having affinity with the impurities and having a higher melting point than the organosilicon compound, melting and mixing while heating, and introducing the impurities into the melted organic wax; obtaining a solidified product of the organic wax by cooling the organic wax; and performing solid/liquid phase separation on the organosilicon compound and the solidified product of the organic wax.

The impurities preferably originate from the organic modifiers used for the modification of the organomodified silicones and organomodified silanes.

The organosilicon compound is preferably a liquid at least at a temperature of 100° C.

The organic wax preferably has a melting point of from 45° C. to 150° C.

The organic wax preferably has an average molecular weight of at least 900.

The organic wax preferably has a (poly)oxyethylene site.

The organosilicon compound preferably has an organomodified group containing a (poly)oxyethylene site.

The silicon atoms of the organosilicon compound can bond with the organomodified group via Si—C bonds or Si—O—C bonds.

The organosilicon compound may be a (poly)oxyethylene group-containing organomodified silicone represented by the following general formula (1):

[Formula 1]

(wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having 9 to 60 carbon atoms, or the chain organosiloxane group represented by the following general formula (2-1):

[Formula 2]

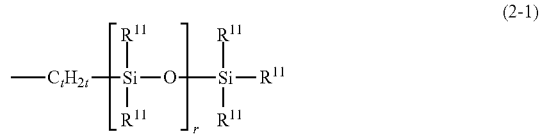

(wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

[Formula 3]

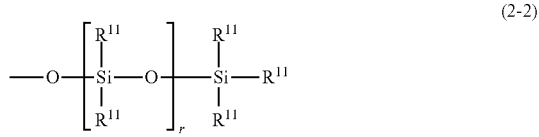

(2-2)

(wherein, $R^{11}$ and r are synonymous with those described above); and $L^1$ represents a silylalkyl group having a siloxane dendron structure expressed by the following general formula (3) when i=1;

[Formula 4]

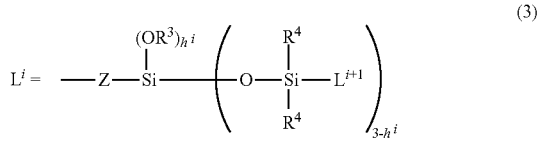

(3)

(wherein the $R^3$ moieties are each independently a substituted or unsubstituted, straight-chain or branched monovalent hydrocarbon group having from 1 to 30 carbon atoms; the $R^4$ moieties are each independently an alkyl group or a phenyl group having from 1 to 6 carbon atoms; Z is a divalent organic group; i is a generation of a silylalkyl group represented by $L^i$ and is an integer from 1 to k when the number of generations serving as a number of repetitions of the silylalkyl group is k; $L^{i+1}$ is the silylalkyl group when i is less than k, and $R^4$ when i=k; and $h^i$ is a number in a range of 0 to 3); Q is a (poly)oxyethylene group-containing organic group; and a, b, c, and d are each numbers in the ranges of $1.0 \le a \le 2.5$, $0 \le b \le 1.5$, $0 \le c \le 1.5$, and $0.0001 \le d \le 1.5$).

The organosilicon compound may be an organomodified silicone obtained by reacting:
(A) an organohydrogenpolysiloxane;
(B) a (poly)oxyethylene group-containing organic compound having one or more reactive unsaturated groups in each molecule; and
(C) one or more types of organic compounds selected from a group consisting of (C1) an organic compound having a number of reactive unsaturated groups greater than 1 on average in each molecule and (C2) an organic compound having one or more reactive unsaturated groups and one or more epoxy groups in each molecule (however, the use of the component (B) is optional when the component (C) contains a (poly)oxyethylene group); the organomodified silicone having a silicon-bonded (poly)oxyethylene group-containing organic group and having a crosslinked structure containing a Si—C bond in a crosslinking part.

The organosilicon compound may be an organomodified silicone in the form of a straight-chain (poly)oxyalkylene group-containing alternating copolymer obtained by reacting at least:
(D) an organopolysiloxane having reactive functional groups at both terminals of a molecular chain; and
(E) an organic compound having two reactive functional groups capable of reacting with the reactive functional groups positioned at both of the molecular chain terminals of the organopolysiloxane (D) in the molecule.

The organosilicon compound has a crosslinked structure containing a Si—O—C chain in the crosslinking part, and the (poly)oxyethylene group-containing organic block constituting the crosslinking part has at least two carbon atom bonds in the organic block and binds to a siloxane block with a chain. The siloxane block consists of siloxane units in which 1 to 3 monovalent organic groups bind to silicon atoms, and the siloxane block has at least two silicon atom bonds so that it can bind to the chain.

The organosilicon compound may be an organomodified silane represented by the following general formula (8):

[Formula 5]

(8)

(wherein $R^{16}$ is a group selected from a hydrogen atom and substituted or unsubstituted, straight-chain or branched monovalent hydrocarbon groups having from 1 to 30 carbon atoms; $X^1$ is a hydrolyzable group selected from alkoxy groups, aryloxy groups, acyloxy groups, secondary amino groups, and aminoxy groups; $Z^1$ is a monovalent organic group differing from $R^{16}$ which is linked to the silicon atoms of general formula (8) by Si—C bonds; $1 \le k \le 3$; $0 \le j \le 2$; and $k+j \le 3$).

In the present invention, the mixture may further contain a solvent of the organosilicon compound.

In addition, in the present invention, the mixture containing the organosilicon compound and the impurities is preferably treated by an acidic aqueous solution, and water and odorizing substances produced by treatment with the acidic aqueous solution are preferably removed by heating or depressurization.

In addition, the object of the present invention is also achieved by an external preparation, a cosmetic, or an industrial material containing a high-purity organosilicon compound obtained by the production method of the present invention.

Advantageous Effects Of Invention

The production method for a high-purity organosilicon compound according to the present invention can be applied regardless of the type of the organic modifier and can reasonably accommodate production on a commercial scale.

In particular, the present invention can stably produce a high-purity organosilicon compound on a commercial scale even when the boiling point of the organic modifier, which is difficult to purify by distillation, is high or the organic modifier is a polymer compound.

In addition, when the mixture contains a solvent of the organosilicon compound, a solution of a high-purity organosilicon compound can be produced easily, and the production of this solution has excellent yield and productivity, so the method is also suitable for production on a commercial scale.

The high-purity organosilicon compound obtained by the production method of the present invention essentially consists of a single component from which impurities—in particular, impurities originating from the organic modifier—have been removed, so phase separation, precipitation of the unreacted starting material, or the like does not occur after production. Therefore, the composition is chemically and physically stable.

In addition, a high-purity organosilicon compound produced by the present invention or a solvent containing the same can be suitably used in external preparations or cosmetics and can further be used widely in various industrial materials.

DESCRIPTION OF EMBODIMENTS

A first aspect of the present invention is a production method for a liquid high-purity organosilicon compound, the method comprising the steps of: adding, to a mixture containing an organosilicon compound selected from a group consisting of organomodified silicones and organomodified silanes and impurities, an organic wax having affinity with the impurities and having a higher melting point than the organosilicon compound, melting and mixing while heating, and introducing the impurities into the melted organic wax; obtaining a solidified product of the organic wax by cooling the organic wax; and performing solid/liquid phase separation on the organosilicon compound and the solidified product of the organic wax.

The production method of the present invention is characterized in that impurities—in particular, impurities originating from an organic modifier—are dissolved in a heated and melted wax, and the organic wax is then solidified by cooling while the impurities remain inside the organic wax. On the other hand, the organosilicon compound is separated from impurities by utilizing the principle that the organosilicon compound is incompatible with the organic wax and remains as a fluid due to its low melting point.

The first aspect of the present invention will be described in detail hereinafter.

≤Production Method for High-purity Organosilicon Compound>

[Organic Wax]

Any organic wax having affinity with impurities—in particular, impurities originating from the organic modifier—and having a higher melting point than the organosilicon compound can be used as the organic wax used in the present invention. The organic wax of the present invention does not contain silicon atoms in its molecular structure. When a solid/liquid separation operation such as filtration is performed at room temperature, the melting point of the organic wax is arbitrary but is preferably at least 45° C. Specifically, the organic wax has a melting point of preferably from 45° C. to 150° C., more preferably from 50° C. to 120° C., and even more preferably from 60° C. to 100° C. and has a number average molecular weight of preferably at least 900, more preferably from 900 to 50,000, and even more preferably from 1,000 to 30,000. When the melting point of the organic wax is lower than 45° C., the melting point of the solid that is produced by cooling after the impurities originating from the organic modifier are introduced becomes even lower, in particular, so in order to perform solid/liquid separation on the solid and the organosilicon compound serving as the main component, it is necessary to perform filtration at a temperature of at most 40° C., for example. Filtration at such a low temperature tends to cause an increase in filtration time when the organosilicon compound is a high-viscosity organomodified silicone, which leads to a risk that the production efficiency may decrease. In addition, a wax with a melting point lower than 45° C. typically has a low capacity to be solidified by introducing impurities, and the solid/liquid separability also tends to be poor. In general, the filtration speed may be low in low-temperature filtration, but filtration may also be performed at around 0° C. or at an even lower temperature by diluting the composition with a solvent such as hexane so as to reduce the viscosity. In addition, the impurity removing effect may be enhanced by performing filtration at a low temperature and aggressively precipitating the solid in accordance with the desired quality, the type of impurities, and the like. On the other hand, when the melting point of the organic wax is higher than 150° C., a larger amount of energy is required to melt the wax, which is not preferable from the perspective of the environment or efficiency. In addition, at a temperature exceeding 150° C., the organosilicon compound itself also typically tends to be diminished, which is not preferable.

Further, when the molecular weight of the organic wax is less than 900, the organic wax tends to become easily compatible with not only impurities originating from the organic modifier, for example, but also with the organosilicon compound modified by the organic modifier serving as the main component, and as a result, the added organic wax blends into the main component, which may make solid/liquid separation difficult. On the other hand, an upper limit is not particularly established for the molecular weight of the organic wax but is ordinarily at most ten million. A high-molecular-weight organic wax may require a special catalyst, equipment, or the like to produce, which may be problematic from the perspective of supply or cost. Therefore, it is preferable to use a composition with a molecular weight of at most 50,000, which is easily procured.

In particular, when the organosilicon compound contains a (poly)oxyethylene site in the molecule, the organic wax preferably has a (poly)oxyethylene site. Examples of organic waxes suitable for such cases include polyethylene glycol (PEG) or polyethylene oxide (PEO) which satisfies the aforementioned conditions related to the melting point and molecular weight, or a compound having a structure of a form in which one or both of the terminal hydroxyl groups thereof are capped with a given sequestering agent. Examples of terminal capping groups include but are not limited to methyl groups, ethyl groups, propyl groups, butyl groups, pentyl groups, hexyl groups, heptyl groups, octyl groups, alkyl groups with even longer chains; cycloalkyl groups such as cyclopentyl groups and cyclohexyl groups; alkenyl groups such as vinyl groups, allyl groups, and butenyl groups; aryl groups such as phenyl groups and tolyl groups; monovalent hydrocarbon groups as typified by aralkyl groups such as benzyl groups; acyl groups such as acetyl groups and benzoyl groups; groups in which the hydrogen atoms bonded to the carbon atoms of these groups are at least partially substituted with organic groups containing hetero atoms; and trimethylsilyl groups. In addition, the organic wax may contain other (poly)oxyalkylene chains or (poly)glycerin chains in addition to the (poly)oxyethylene chain within a range that does not diminish the effect of the present invention. Further, the organic wax may be a compound of a form in which multiple ethylene oxides are addition-polymerized with various polyhydric alcohols or a compound using such a compound as a base.

When the organosilicon compound contains both a (poly)oxyethylene site and a (poly)oxypropylene site in the molecule or has a structure not containing a (poly)oxyalkylene site other than the (poly)oxypropylene site, the organic wax preferably has structural units in which a (poly)oxyethylene site and a (poly)oxypropylene site are connected in blocks. These blocks may repeat or may form a non-repeating AB-type or ABA-type block copolymer. Examples of organic waxes suitable for such cases include a polyethylene glycol (PEG)/polypropylene glycol (PPG) copolymer or polyethylene oxide (PEO)/polypropylene glycol (PPG)

copolymer which satisfies the aforementioned conditions related to the melting point and molecular weight, or a compound having a structure of a form in which one or both of the terminal hydroxyl groups thereof are capped with a given sequestering agent. Examples of terminal capping groups include but are not limited to those described above. In addition, the organic wax may contain other (poly) oxyalkylene sites or (poly)glycerin sites in addition to the (poly)oxyethylene site and the (poly)oxypropylene site within a range that does not diminish the effect of the present invention. Further, the organic wax may be a compound of a form in which ethylene oxides and propylene oxides are addition-polymerized with various polyhydric alcohols or a compound using such a compound as a base.

A suitable amount of the organic wax that is used is from 0.1 to 10 wt. % and more preferably from 0.5 to 5 wt. % with respect to the organosilicon compound serving as the main component. At less than 0.1 wt. %, the effect of removing impurities is often insufficient. When the amount used exceeds 10 wt. %, it is not only economically disadvantageous, but the filter efficiency or yield also decreases, and there is often waste from the perspective of the impurity removing effect.

A reaction mixture containing an organosilicon compound as a main component and impurities—in particular, components derived from an organic modifier serving as one of the starting materials of the organosilicon compound—as impurities has affinity with the impurities, and the aforementioned organic wax having a higher melting point than the organosilicon compound is added, heated, melted, and mixed. Mixing is preferably performed using mechanical power. For example, mixing can be performed with a paddle mixer, a propeller mixer, or in a reaction vessel or a container equipped with mixing blades, and an emulsifier, a kneader, or the like may also be used as necessary. In addition, the mixing of both components must be performed at a temperature equal to or higher than the temperature at which the organic wax that is used melts, and from the perspective of dissolving and introducing the impurities into the melted wax, it is preferably performed sufficiently so that the entire composition is thoroughly mixed. At this time, when the organosilicon compound has high viscosity and treatment is performed by adding a solvent which is a good solvent for the organosilicon compound and a poor solvent for the impurities, the viscosity of the system decreases, so the contact between the impurities and the organic wax component occurs efficiently, and as a result, the introduction of impurities by means of the organic wax (that is, the increase in the purity of the organosilicon compound) can be accelerated. Ordinarily, mixing and stifling should be performed for 5 minutes to 5 hours and preferably from 30 minutes to 2 hours in a range of from 45 to 150° C. and preferably from 70 to 120°. Treatment can be completed in a shorter amount of time when the capacity of the mixer/stirrer is higher, but the treatment conditions can be set out of consideration of the energy cost such as the power consumption. The mixture is then left to cool or is cooled so as to be integrally solidified (preferably as solid particles) while impurities remain in the wax, whereas the organosilicon compound serving as the main component in the system is incompatible with the organic wax and remains as a fluid due to its low melting point. In this cooling process, the stifling and mixing operation may or may not be performed. It is also possible, in principle, to perform the mixing operation and the like using human or animal power, but this is not advantageous from the perspective of stable production or efficiency on an industrial scale.

The mixture containing the organosilicon compound fluid and solid particles obtained by the treatment process described above can be subjected to liquid/solid separation by means of a common filtration operation with filter paper using diatomaceous earth, activated carbon, or the like, as a filter aid, for example. This makes it possible to easily obtain a high-purity organosilicon compound. When a solvent which is a good solvent for the organosilicon compound and a poor solvent for the impurities is used in the treatment process, a mixture containing the organosilicon compound fluid, the solid particles, and the solvent is subjected to solid/liquid separation by means of a filtration operation with filter paper using diatomaceous earth, activated carbon, or the like, as a filter aid, for example. When the solvent can be used as an oil agent for a cosmetic, for example, the filtrate can be used as a cosmetic starting material containing a high-purity organosilicon compound and an oil agent and formed into a product directly. On the other hand, when a volatile substance is used as the solvent, a high-purity organosilicon compound can be obtained by removing the volatile solvent by means of a heating and depressurization operation or the like from the filtrate after solid/liquid separation. When the organosilicon compound has high viscosity, performing treatment with the organic wax in the presence of the solvent is advantageous for an increase in purity or a decrease in turbidity of the organosilicon compound.

[Organosilicon Compound]

The organosilicon compound to which the present invention can be applied is a liquid composition and is preferably a liquid at least at a temperature of 100° C.

In the present invention, a "liquid form" or a "liquid" means that after the liquid surface of an organopolysiloxane in a prescribed container is placed horizontally and the vessel is then inclined, the liquid surface can once again become horizontal after 1 hour, preferably after 30 minutes, and more preferably after 10 minutes. Here, "horizontal" means to form a plane that intersects the direction of gravitational force at a right angle. The organosilicon compound is preferably a liquid at least at 100° C. but more preferably also exhibits liquidity in a range of 100° C. or less to room temperature. Specifically, the glycerin derivative-modified silicone is preferably a liquid at 80° C., more preferably a liquid at 40° C., and even more preferably a liquid at room temperature (25° C.). Compositions with liquidity at a temperature of 100° C. or higher are, of course, included in the scope of liquid organic silicon compounds, but even compounds which are in a semi-gelatinous form or a soft solid form without fluidity at room temperature (25° C.) or lower but demonstrate liquidity when heated to 100° C., for example, are also included.

The organosilicon compound is selected from a group consisting of organomodified silicones and organomodified silanes.

The organomodified silicones and organomodified silanes are modified by organic modifiers. For example, when the organosilicon compound has a (poly)oxyethylene group, the organosilicon compound is modified by an organic modifier having a (poly)oxyethylene group. Further, the impurities preferably originate from the organic modifier.

A compound having a (poly)oxyalkylene site can be suitably used as the organosilicon compound. Examples of the (poly)oxyalkylene include (poly)oxyethylene, (poly)oxypropylene, (poly)oxybutylene, or combinations thereof, but (poly)oxyethylene, (poly)oxypropylene, or combinations thereof are preferable, and (poly)oxyethylene is more preferable.

(Organomodified Silicone)

The organosilicon compound may be a (poly)oxyethylene group-containing organomodified silicone represented by the following general formula (1):

[Formula 6]

$$R^1{}_a R^2{}_b L^1{}_c Q_d SiO_{(4-a-b-c-d)/2} \quad (1)$$

wherein
$R^1$ is a monovalent organic group (however, excluding $R^2$, $L^1$, and Q), a hydrogen atom, or a hydroxyl group; and
$R^2$ is a substituted or unsubstituted, straight-chain or branched monovalent hydrocarbon group having from 9 to 60 carbon atoms,
or a chain organosiloxane group represented by the following general formula (2-1):

[Formula 7]

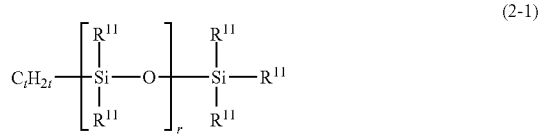

(2-1)

(wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

[Formula 8]

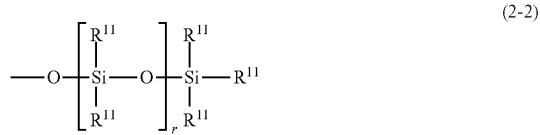

(2-2)

(wherein, $R^{11}$ and r are synonymous with those described above); and $L^1$ represents a silylalkyl group having a siloxane dendron structure expressed by the following general formula (3) when i=1;

[Formula 9]

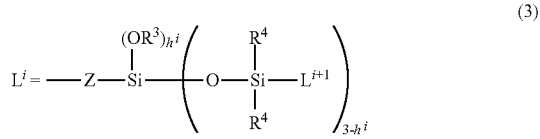

(3)

(wherein
the $R^3$ moieties are each independently a substituted or unsubstituted, straight-chain or branched monovalent hydrocarbon group having from 1 to 30 carbon atoms;
$R^4$ moieties each independently represents an alkyl group or a phenyl group having from 1 to 6 carbon atoms;
Z is a divalent organic group;
i is a generation of a silylalkyl group represented by $L^i$ and is an integer from 1 to k when the number of generations serving as a number of repetitions of the silylalkyl group is k; $L^{i+1}$ is the silylalkyl group when i is less than k, and $R^4$ when i=k; and $h^i$ is a number in a range of 0 to 3);
Q is a (poly)oxyethylene group-containing organic group; and
a, b, c, and d are each numbers in the ranges of $1.0 \le a \le 2.5$, $0 \le b \le 1.5$, $0 \le c \le 1.5$, and $0.0001 \le d \le 1.5$).

Here, if the (poly)oxyethylene group-containing organomodified silicone represented by general formula (1) has the long chain organic group or the chain organosiloxane group represented by $R^2$, b is a number greater than 0, preferably $0.0001 \le b \le 1.5$, and more preferably $0.001 \le b \le 1.5$. Similarly, when the (poly)oxyethylene group-containing organomodified silicone represented by general formula (1) has a silylalkyl group having a siloxane dendron structure represented by the aforementioned $L^1$, c is a number greater than 0, preferably $0.0001 \le c \le 1.5$, and more preferably $0.001 \le c \le 1.5$.

The (poly)oxyethylene group-containing organomodified silicone preferably has a long-chain organic group or a chain organosiloxane group represented by $R^2$ or a silylalkyl group having a siloxane dendron structure represented by $L^1$ together with the (poly)oxyethylene group-containing organic group serving as Q.

At this time, the suitable values of b and c are expressed as follows by essential functional groups.
(1) When there is a group represented by $R^2$: $0.001 \le b \le 1.5$ and $0 \le c \le 1.5$.
(2) When there is a group represented by $L^1$: $0 \le b \le 1.5$ and $0.001 \le c \le 1.5$.
(3) When there are both a group represented by $R^2$ and a group represented by $L^1$: $0.001 \le b \le 1.5$ and $0.001 \le c \le 1.5$.

The monovalent groups represented by $R^1$ in general formula can be the same or different and are not particularly limited as long as they are not the functional groups of $R^2$, $L^1$, and Q. However, they are preferably a substituted or unsubstituted, straight-chain or branched monovalent hydrocarbon group having from 1 to 8 carbon atoms, a (poly) oxyalkylene group represented by —$R^5O(AO)_nR^6$ (wherein, AO represents an oxyalkylene group having from 3 to 4 carbon atoms; $R^5$ represents a substituted or unsubstituted, straight-chain or branched divalent hydrocarbon group having from 3 to 5 carbon atoms; $R^6$ represents a substituted or unsubstituted, straight-chain or branched monovalent hydrocarbon group having from 1 to 24 carbon atoms and hydrogen atoms or a substituted or unsubstituted, straight-chain or branched acyl group having from 2 to 24 carbon atoms; and n is from 1 to 100), an alkoxy group, a hydroxyl group, or a hydrogen atom. However, not all of the $R^1$ moieties are hydroxyl groups, hydrogen atoms, alkoxy groups, or (poly) oxyalkylene groups.

Examples of a monovalent hydrocarbon group having from 1 to 8 carbon atoms are, for example, alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group having an epoxy group, a glycidyl group, an acyl group, a carboxyl group, an amino group, a (meth)acryl group, a mercapto group, or the like (however, the total number of carbon atoms is from 1 to 8). The monovalent hydrocarbon group is preferably a group other than an alkenyl group, and is particularly preferably a methyl group, an ethyl group, or a phenyl group. Additionally, examples of the alkoxy group include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Particularly, the $R^1$ moieties are preferably monovalent hydrocarbon groups having from 1 to 8 carbon atoms and that are free of unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 mol % to 100 mol % of all the $R^1$ moieties are selected from methyl groups, ethyl groups, or phenyl groups.

It is possible to introduce or design a modified group other than a hydrophilic group (-Q), particularly a short chain or medium chain hydrocarbon based group, into the (poly) oxyethylene group-containing organomodified silicone as $R^1$ with the objective of imparting additional functionality. Specifically, when $R^1$ is a substituted monovalent hydrocarbon group, a substituent can be preferably selected in accordance with desired characteristics and uses. For example, when using the glycerin derivative-modified silicone as a cosmetic composition or a fiber treating agent starting material, it is possible to introduce an amino group, amide group, aminoethyl aminopropyl group, carboxyl group, and the like, as the substituted group of a monovalent hydrocarbon group, for the purpose of improving the sensation during use, feeling to touch, persistence, and the like.

The substituted or unsubstituted, straight or branched monovalent hydrocarbon group having from 9 to 60 carbon atoms of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the (poly)oxyethylene group-containing organomodified silicone, it is preferable for some or all of the $R^2$ moieties to be monovalent long-chain hydrocarbon groups, and by having such monovalent long-chain hydrocarbon groups in the molecule, the (poly) oxyethylene group-containing organomodified silicone exhibits superior compatibility not only with silicone oils, but also with non-silicone oils having a high alkyl group content. For example, it is possible to obtain an emulsion and a dispersion containing non-silicone oils with excellent thermal stability and stability over time.

Substituted or unsubstituted, straight or branched monovalent hydrocarbon groups that are represented by $R^2$ of general formula (1), that are bonded to silicon atoms, and that have 9 to 60 carbon atoms, may be the same or different. Furthermore, the structure thereof is selected from among straight chain, branched, and partially branched. In the present invention, it is particularly preferable for R2 to be an unsubstituted straight chain monovalent hydrocarbon group. An unsubstituted monovalent hydrocarbon group can be, for example, an alkyl group, aryl group, or aralkyl group having from 9 to 60 carbon atoms, preferably from 9 to 30 carbon atoms, and more preferably from 10 to 25 carbon atoms. On the other hand, examples of the substituted monovalent hydrocarbon group include perfluoroalkyl groups, aminoalkyl groups, amide alkyl groups, and ester groups having from 9 to 30 carbon atoms, preferably from 9 to 30 carbon atoms, and more preferably from 10 to 24 carbon atoms. Additionally, the carbon atoms of the monovalent hydrocarbon groups may be partially substituted with alkoxy groups, and examples of said alkoxy groups include methoxy groups, ethoxy groups, and propoxy groups. This type of monovalent hydrocarbon group is particularly preferably an alkyl group having 9 to 30 carbon atoms, and an example thereof is a group represented by the general formula —$(CH_2)_v$—$CH_3$ (v is a number in a range of 8 to 29). Particularly, an alkyl group having from 10 to 24 carbon atoms is preferable.

The chain organosiloxane group in general formula (2-1) or (2-2) has a straight chain polysiloxane chain structure, unlike a silylalkyl group, which has a siloxane dendron structure. In general formula (2-1) or (2-2), $R^{11}$ are each independently a substituted or unsubstituted monovalent hydrocarbon group having from 1 to 30 carbon atoms, a hydroxyl group, or a hydrogen atom. The substituted or unsubstituted monovalent hydrocarbon group having from 1 to 30 carbon atoms is preferably an alkyl group having from 1 to 30 carbon atoms, an aryl group having from 6 to 30 carbon atoms, an aralkyl group having from 6 to 30 carbon atoms, or a cycloalkyl group having from 6 to 30 carbon atoms, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbon atoms is also preferable.

In general formula (2-1) or (2-2), t is a number in a range of 2 to 10; r is a number in a range of 1 to 500; and r preferably is a number in a range of 2 to 500. Such a straight chain organosiloxane group is hydrophobic. From the standpoint of compatibility with various oil agents, r preferably is a number in a range of 1 to 100, and particularly preferably is a number in a range of 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external preparation or cosmetic that incorporates the (poly)oxyethylene group-containing organomodified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having from 1 to 30 carbon atoms (the $R^3$ moieties in general formula (3)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbon atoms is from 1 to 30).

Among the phenyl group or the alkyl group having from 1 to 6 carbon atoms represented by $R^4$ in general formula (3), examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight, branched, or cyclic alkyl groups.

In the aforementioned general formula (3), in the case of i=k, $R^4$ is preferably a methyl group or a phenyl group. In particular, R4 is preferably a methyl group when i=k.

From an industrial standpoint, the number of generations k is preferably an integer from 1 to 3, and more preferably is 1 or 2. In each of the number of generations, the group represented by $L^1$ is expressed as follows. In the formulae, $R^3$, $R^4$, and Z are the same groups as described above.

When the number of generations is k=1, $L^1$ is expressed by the following general formula (3-1).

[Formula 10]

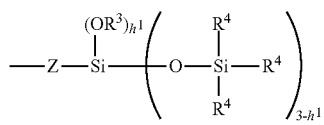

(3-1)

When the number of generations is k=2, $L^1$ is expressed by the following general formula (3-2).

[Formula 11]

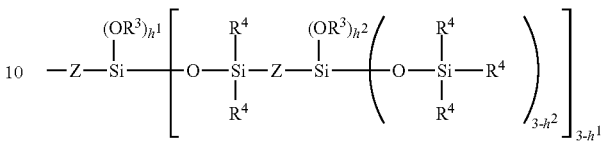

(3-2)

When the number of generations is k=3, $L^1$ is expressed by the following general formula (3-3).

[Formula 12]

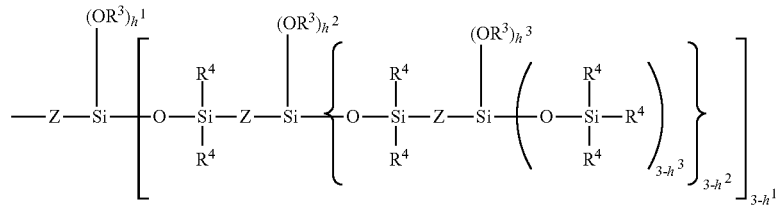

(3-3)

In the structures expressed by the general formulae (3-1) to (3-3) in the case of the number of generations is from 1 to 3, each of $h^1$, $h^2$ and $h^3$ moieties is independently a number in a range of 0 to 3. These $h^i$ moieties are preferably a number in a range of 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups expressed by the following general formula.

[Formula 13]

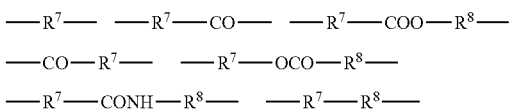
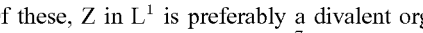

Of these, Z in $L^1$ is preferably a divalent organic group expressed by general formula —$R^7$— that is introduced by a reaction between a silicon-bonded hydrogen atom and an alkenyl group. Likewise, Z is preferably a divalent organic group expressed by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is 2 or more, and $L^i$ is $L^2$ to $L^k$, Z is preferably an alkylene group having from 2 to 10 carbon atoms or a divalent organic group represented by $-R^7-COO-R^8-$ and is particularly preferably a group selected from an ethylene group, a propylene group, a methylethylene group, a hexylene group, and $-CH_2C(CH_3)COO-C_3H_6-$.

In the general formula described above, $R^7$ are each independently a substituted or unsubstituted straight or branched chain alkylene group or alkenylene group having from 2 to 22 carbon atoms or an arylene group having from 6 to 22 carbon atoms. More specifically, examples of $R^7$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^8$ is preferably a group selected from an ethylene group, a propylene group, a methylethylene group, and a hexylene group.

In the general formula described above, $R^8$ is a group selected from divalent organic groups expressed by the following formula.

[Formula 14]

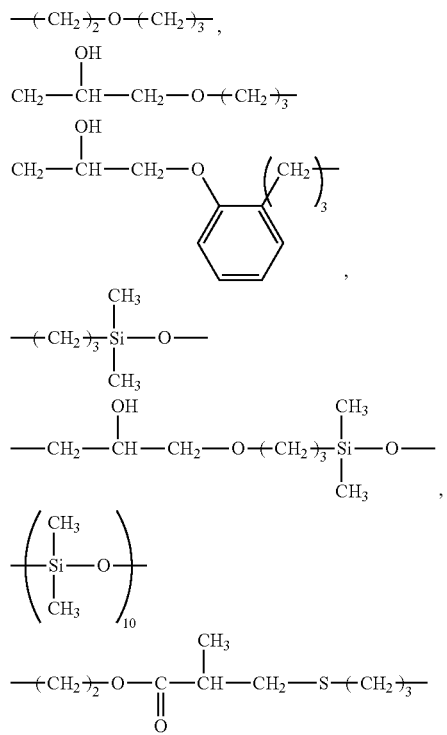

In general formula (1), Q is a (poly)oxyethylene group-containing organic group and constitutes the hydrophilic site of the (poly)oxyethylene group-containing organomodified silicone. The structure of Q is not limited provided that the structure has a (poly)oxyethylene site, but the (poly)oxyethylene site is preferably bonded to a silicon atom via a divalent organic group.

The (poly)oxyethylene group-containing organic group is a hydrophilic group having a (poly)oxyethylene structure and preferably has a unit represented by the formula: $-(C_2H_4O)_{t1}(C_3H_6O)_{t2}(C_4H_8O)_{t3}-$ (wherein t1, t2, and t3 are numbers satisfying 1≤t1≤100, 0≤t2≤100, and 0≤t3≤50, preferably numbers satisfying 1≤t1≤50, 0≤t2≤50, and 0≤t3≤30, and more preferably numbers satisfying 1≤t1≤30, 0≤t2≤30, and 0≤t3≤10). In addition, some or all of the terminal hydroxyl groups thereof may be capped by an alkyl group, an acyl group, or the like. Furthermore, the (poly)oxyethylene structure may be straight or branched, and may be a structure that is branched in a dendritic manner as well.

Such a (poly)oxyethylene group-containing organic group (Q) may be a (poly)oxyethylene group-containing organomodified silicone which bonds to silicon atoms via a linking group that is at least divalent and contains at least one type of hydrophilic unit selected from hydrophilic units represented by the following structural formulae (3-3) to (3-6).

[Formula 15]

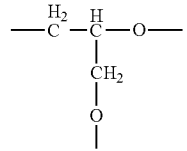 (3-3)

[Formula 16]

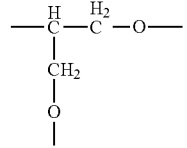 (3-4)

[Formula 17]

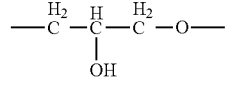 (3-5)

[Formula 18]

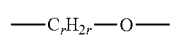 (3-6)

$-C_rH_{2r}-O-$

In structural formula 3-1, r is a number in a range of 1 to 6.

In formulae (3-3) to (3-5), W is a hydrogen atom or an alkyl group having from 1 to 20 carbon atoms, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (3-3) to (3-5) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups.

In general formula (1), Q may be a hydrophilic group having a branched structure in part of the functional group.

For example, the (poly)oxyethylene group-containing organic group (Q) may be a (poly)oxyethylene group-containing organic group which bonds to silicon atoms via a linking group that is at least divalent and has at least one type of hydrophilic unit selected from hydrophilic units represented by the above structural formulae (3-3) to (3-6) forming a bond as a straight chain. Similarly, Q may be a (poly)oxyethylene group-containing organic group that is bonded to a silicon atom via a linking group that is at least divalent, the (poly)oxyethylene group-containing organic group containing at least one type of hydrophilic unit selected from hydrophilic units represented by the above structural formulae (3-3) to (3-6) and having a branched unit selected from groups represented by the following structural formulae (3-7) to (3-9).

[Formula 19]

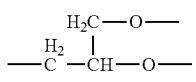
(3-7)

[Formula 20]

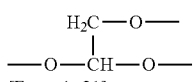
(3-8)

[Formula 21]

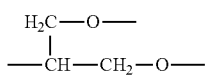
(3-9)

The at least one type of hydrophilic unit selected from the hydrophilic units represented by the general formulae (3-3) to (3-6) are each independently bonded to the two oxygen atoms of the above structural formulae (3-7) to (3-9). The hydrophilic unit may further be bonded to a branch unit selected from groups represented by structural formulae (3-7) to (3-9). Moreover, the hydrophilic unit may be formed so as to have a dendroid-shape polyether structure obtained by branching into multiple generations.

The linking group that is at least divalent is a bonding site with respect to the silicon atom included in the hydrophilic group (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

[Formula 22]

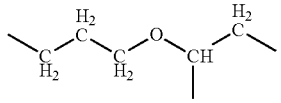

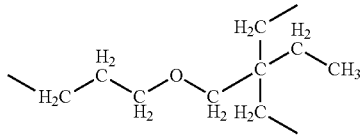

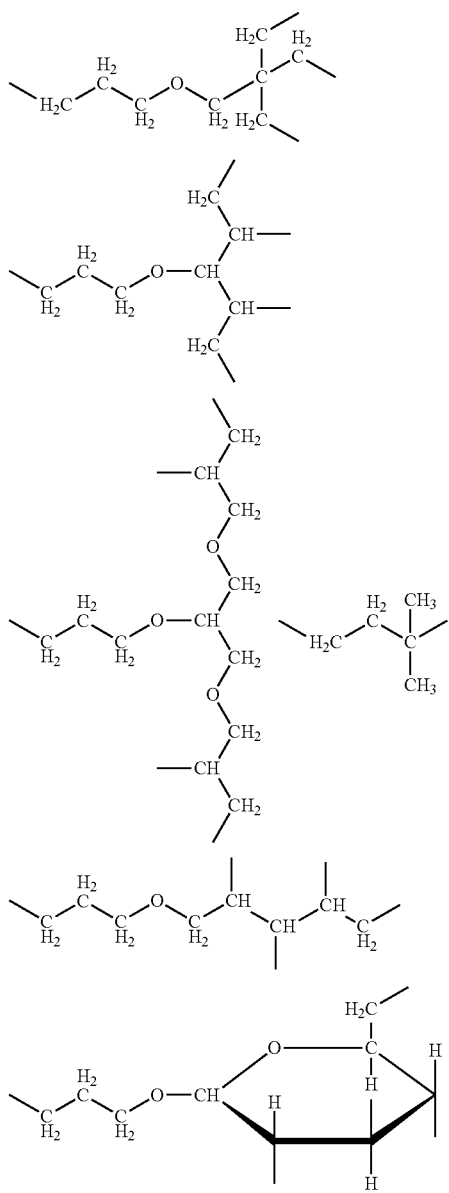

More preferably, Q is a hydrophilic group represented by the following structural formulae (4-1) to (4-4).

[Formula 23]

(4-1)

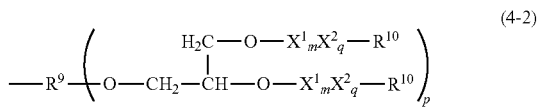
(4-2)

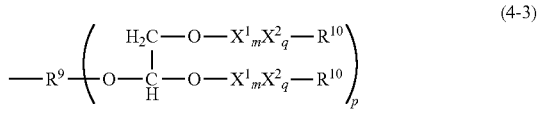
(4-3)

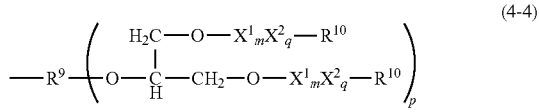

$$(4\text{-}4)$$

In formulae (4-1) to (4-4), $R^9$ is an organic group having (p+1) valence, and p is a number that is greater than or equal to 1 and less than or equal to 3. As the aforementioned $R^9$, the same groups as the aforementioned linking groups having two or more valences may be mentioned.

It is more preferable that p is equal to 1 and that $R^9$ is a group selected from divalent organic groups expressed by the following general formulae.

[Formula 24]

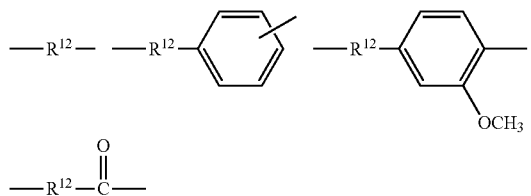

In the formulae, $R^{12}$ may have a substituent, and are each independently a straight or branched chain alkylene group or alkenylene group having from 2 to 22 carbon atoms, or an arylene group having from 6 to 22 carbon atoms.

$X^1$ are each independently at least one hydrophilic unit selected from the hydrophilic units expressed by general formulae (3-3-1) to (3-5-1) below, and m is a number in a range of 0 to 5, and is more preferably a number in a range of 0 to 3.

[Formula 25]

$$(3\text{-}3\text{-}1)$$

[Formula 26]

$$(3\text{-}4\text{-}1)$$

[Formula 27]

$$(3\text{-}5\text{-}1)$$

$X^2$ is a (poly)oxyethylene unit, and q is a number in a range of 1 to 100. q is preferably a number within a range of 1 to 50 and is more preferably from 1 to 30. $X^2$ may contain a (poly)oxypropylene unit and/or a (poly)oxybutylene unit together with the (poly)oxyethylene unit. In this case, $X^2$ may be contained in Q is a (poly)oxyalkylene group represented by the formula: $-(C_2H_4O)_{t1}(C_3H_6O)_{t2}(C_4H_8O)_{t3}-$ (in the formula, t1, t2, and t3 are numbers satisfying $1 \leq t1 \leq 100$, $0 \leq t2 \leq 100$, and $0 \leq t3 \leq 50$, preferably numbers satisfying $1 \leq t1 \leq 50$, $0 \leq t2 \leq 50$, and $0 \leq t3 \leq 30$, and more preferably numbers satisfying $1 \leq t1 \leq 30$, $0 \leq t2 \leq 30$, and $0 \leq t3 \leq 10$).

Here, the manner in which $X^1$ and $X^2$ are bonded can be block or random. That is, the hydrophilic group Q may be a hydrophilic group in which hydrophilic segments, which are obtained by bonding hydrophilic units expressed by general formulae (3-3-1) to (3-5-1) above in a block manner, are bonded to hydrophilic segments comprising (poly)oxyalkylene units, and may be a hydrophilic group in which these constituent units are bonded in a random manner. An example thereof is a bonding pattern such as $-(X^2)_{m1}-X^1-(X^2)_{m2}-X^1-$.

$R^{10}$ is a hydrogen atom or a group selected from the group consisting of glycidyl groups, acyl groups, and alkyl groups having from 1 to 20 carbon atoms.

The (poly)oxyethylene group-containing organomodified silicone having a (poly)oxyethylene group-containing organic group (-Q) represented by general formula (1) is preferably a liquid at least at 100° C. In addition, the polysiloxane main chain may be a straight chain, a branched chain, or reticulated (including slightly crosslinked and elastomeric). With the production method of the present invention, it is possible to easily improve the opaque appearance of a composition and stabilize the composition as a translucent or transparent uniform liquid, not only in the case of a low-viscosity (poly)oxyethylene group-containing organomodified silicone, but also in the case of a (poly)oxyethylene group-containing organomodified silicone which has high viscosity and is in a solid form at room temperature (including gummy compositions having plasticity and poor fluidity).

The (poly)oxyethylene group-containing organomodified silicone is particularly preferably a (poly)oxyethylene group-containing organomodified silicone having a straight-chain polysiloxane structure represented by the following structural formula (1-1):

[Formula 28]

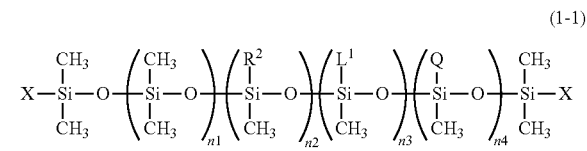

$$(1\text{-}1)$$

(In the formula,
$R^2$, $L^1$, and Q are each independently synonymous with those described above;
X is a group selected from among the groups comprising a methyl group, $R^2$, $L^1$, and Q;
n1, n2, n3, and n4 are each independently a number in a range of 0 to 2,000, and n1+n2+n3+n4 is a number in a range of 0 to 2,000; however, when n4=0, at least one X is Q).

In formula (1-1), (n1+n2+n3+n4) preferably is a number in a range of 10 to 2,000, more preferably is in a range of 25 to 1,500, and particularly preferably is a number in a range of 50 to 1,000. n1 preferably is a number in a range of 10 to 2,000, more preferably is in a range of 25 to 1,500, and particularly preferably is in a range of 50 to 1,000. n2 preferably is a number in a range of 0 to 250, more preferably in a range of 0 to 150.

When $R^2$ is the aforementioned long chain alkyl group, n2>1 is particularly preferable from the standpoint of compatibility with oil agents other than silicone and surface activity. n3 preferably is a number in a range of 0 to 250, and it is particularly preferable that 3>1, and that it has least one silylalkyl group (—$L^1$) having a siloxane dendron structure in a side chain portion. n4 is a number in a range of 0 to 100, and preferably is in a range of 0 to 50. However, when n4=0, at least one X must be Q.

In the aforementioned structural formula (1-1), it is preferable for each Q to independently be a (poly)oxyethylene group-containing organic group represented by any of general formulae (4-1) to (4-4). In the (poly)oxyethylene group-containing organomodified silicone, all Q moieties may be one type of (poly)oxyethylene group-containing organic group represented by any of general formulae (4-1) to (4-4), or some of the Q moieties in each molecule may be (poly)oxyethylene group-containing organic groups represented by any of the general formulae (4-1) to (4-4), and the remaining Q moieties may be other (poly)oxyethylene group-containing organic groups.

Further, the (poly)oxyethylene group-containing organomodified silicone may be one type or a mixture of two or more types of (poly)oxyethylene group-containing organomodified silicones represented by general formula (1). More specifically, the silicone can be a mixture of at least two types of (poly)oxyethylene group-containing organomodified silicones, with different types of modified groups, modification rate, and degree of polymerization of the siloxane main chain.

The (poly)oxyethylene group-containing organomodified silicone is more preferably a (poly)oxyethylene group-containing organomodified silicone represented by the following structural formula (1-1-1):

[Formula 29]

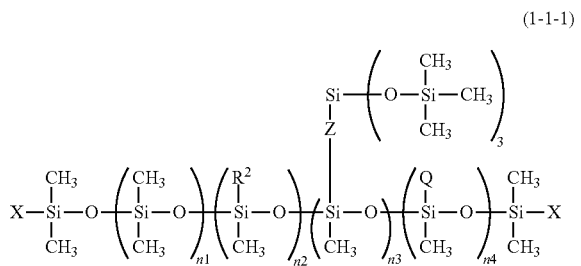

(1-1-1)

(wherein
(In the formula, $R^2$, Q, X, Z, n1, n2, n3, and n4 are synonymous with those described above), or the following structural formula (1-1-2):

[Formula 30]

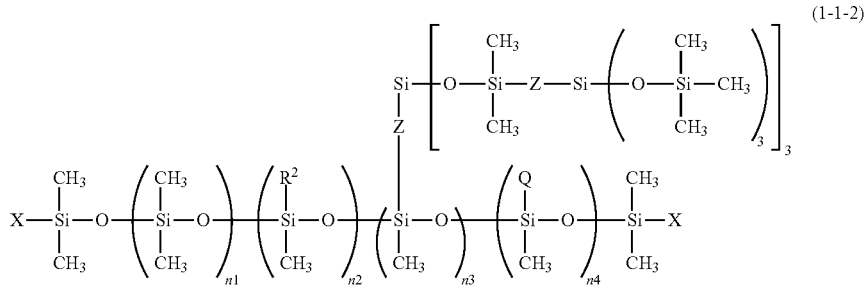

(1-1-2)

(wherein
$R^2$, Q, X, Z, n1, n2, n3, and n4 are synonymous with those described above).

The modification rate of organopolysiloxane due to the (poly)oxyethylene group-containing organic group is preferably in a range of 0.001 to 50 mol %, more preferably within the range of 0.01 to 30 mol %, and yet more preferably within the range of 0.1 to 10 mol % of all functional groups bonded to polysiloxane, which is the main chain. Furthermore, in the (poly)oxyethylene group-containing organomodified silicone represented by structural formula (1-1), the modification rate (mol %) resulting from the (poly)oxyethylene group-containing organic group is expressed by the following formula:

Modification rate (mol %)=(number of (poly)oxyethylene group-containing organic groups bonded to silicon atoms per molecule)/(6+2×(n1+n2+n3+n4))×100

For example, in the case of a (poly)oxyethylene group-containing organomodified silicone containing dodecylsiloxane having ten (poly)oxyethylene group (POE group)-containing organic groups (represented by the structural formula $MD^{POE}_{10}M$), 10 out of the 26 silicon-bonded functional groups are modified by the (poly)oxyethylene group-containing organic groups, so the modification rate by the (poly)oxyethylene group-containing organic group is 38.5 mol %.

(Production of (poly)oxyethylene Group-containing Organomodified Silicone and Mixture Containing the Same as a Main Component)

The (poly)oxyethylene group-containing organomodified silicone can be obtained by, for Example, reacting (a1) a (poly)oxyethylene derivative having one reactive unsaturated group per molecule, (b1) organopolysiloxane having silicon atom bonded hydrogen atoms, and (c1) an organic compound having one reactive unsaturated group per molecule, and if necessary, (d1) a siloxane dendron compound having one reactive unsaturated group per molecule, and/or (e1) a long chain hydrocarbon compound or a chain organopolysiloxane compound having one reactive unsaturated group per molecule in the presence of a hydrosilylation reaction catalyst. The reactive unsaturated group preferably is an unsaturated functional group having a carbon-carbon double bond, and is exemplified by an alkenyl group or unsaturated fatty acid ester group. The —$R^1$ is introduced by component (c1), the —$L^1$ is introduced by component (d1), and the id —$R^2$ is introduced by component (e1).

More specifically, a (poly)oxyethylene group-containing organomodified silicone can be obtained as follows, for example.

The (poly)oxyethylene group-containing organomodified silicone can be obtained by addition reacting with organopolysiloxane having a silicon-hydrogen bond, an unsaturated organic compound having a carbon-carbon double bond at one terminal of the molecular chain, and an unsaturated ether compound of a (poly)oxyethylene derivative having a carbon-carbon double bond in the molecule. Furthermore, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain can be further addition reacted.

In the above case, the (poly)oxyethylene group-containing organomodified silicone can be obtained as the product of a hydrosilylation reaction between the unsaturated organic compound and the (poly)oxyethylene derivative unsaturated ether compound, and optionally the siloxane dendron compound and/or an unsaturated long chain hydrocarbon compound, or a chain organopolysiloxane having a carbon-carbon double bond at one terminal of the molecular chain and a SiH group-containing siloxane. This enables the introduction of an organic group and a(poly)oxyethylene group-containing organic group, and optionally a silylalkyl group having a siloxane dendron structure and/or a long chain hydrocarbon group or a chain organopolysiloxane group into the polysiloxane chain of the (poly)oxyethylene group-containing organomodified silicone. This reaction can be performed as a batch or can take the form of successive reactions. However, successive reactions are preferable from the perspectives of safety and quality control.

The (poly)oxyethylene group-containing organomodified silicone can be obtained by, for example, reacting at least: (b2) an organohydrogensiloxane represented by the following general formula (1'):
[Formula 31]

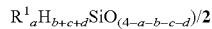

(1')

(wherein
R¹, a, b, c, and d are synonymous with those described above); and (a2) a (poly)oxyethylene derivative having one reactive unsaturated group per molecule in the presence of a hydrosilylation reaction catalyst. It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

The (poly)oxyethylene group-containing organomodified silicone can be preferably produced by reacting together component (a2), component (d) and/or component (e), as well as (b2) an organohydrogensiloxane expressed by general formula (1'), or by successively addition-reacting the organohydrogensiloxane (b2) and discretionally the component (d), and/or the component (e), and further-addition reacting the component (a2), in a state in which (a2) a (poly)oxyethylene derivative having one reactive unsaturated group per molecule, and optionally (d) a siloxane dendron compound having one reactive unsaturated group per molecule, and/or (e) a hydrocarbon compound having one reactive unsaturated group per molecule or a chain organopolysiloxane having one reactive unsaturated group per molecule coexist.

The organohydrogensiloxane (b2) used in the synthesis of the (poly)oxyethylene group-containing organomodified silicone is preferably an organohydrogensiloxane represented by, for example, the following structural formula (1-1)':

[Formula 32]

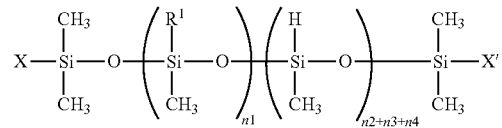

(1-1)'

(wherein
(In the formula, R¹ are each independently synonymous with that described above;
X' is a group selected from R¹ or hydrogen atom; and
n1, n2, n3, and n4 are synonymous with those described above; however, when n2+n3+n4=0, at least one X' is a hydrogen atom)

The (poly)oxyethylene group-containing organomodified silicone is preferably synthesized by subjecting to a hydrosilylation reaction (a) a (poly)oxyethylene derivative having a carbon-carbon double bond at a terminal of the molecular chain, and (b) an organohydrogenpolysiloxane; and the organohydrogensiloxane (component (b) is preferably the organohydrogensiloxane obtained by successively addition-reacting the component (d1) and/or the component (e1). In this case, the organohydrogensiloxane immediately prior to reaction with component (a) (after successive reactions with other components) is preferably represented by the following structural formula (1-1A).

[Formula 33]

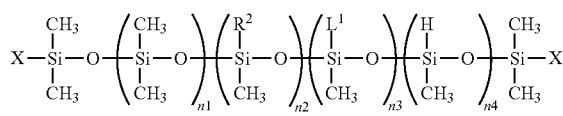

(1-1A)

(wherein
R² and L¹ are each independently synonymous with those described above;
X is selected from the groups comprising a methyl group, R², L¹, and a hydrogen atom (H);
n1, n2, n3, and n4 are each independently a number in a range of 0 to 2,000, and n1+n2+n3+n4 is a number in a range of 0 to 2,000; however, when n4=0, at least one X is a hydrogen atom.)

The (poly)oxyethylene derivative having one reactive unsaturated group per molecule, which is used in the synthesis of the (poly)oxyethylene group-containing organomodified silicone, is preferably (a) a (poly)oxyethylene derivative having a carbon-carbon double bond at the terminal of the molecular chain. These are (poly)oxyethylene derivatives having a reactive functional group such as an alkenyl group at the molecular chain terminal, such as an allyl (poly)oxyethylene, and can be synthesized according to a known method.

In the (poly)oxyethylene group-containing organomodified silicone, from the perspective of the performance as a surfactant (emulsifier) and various treatment agents (powder dispersing agents or surface treatment agents) or usage as a cosmetic starting material, the component (a) is, specifically, preferably a (poly)oxyethylene monoallyl ether, and from the perspective of the thickening effect on the oil agent components, the gelification capacity, the performance of the surfactant (emulsifier), or usage as a cosmetic starting material, the component (a) is, specifically, preferably a (poly)oxyethylene (poly)oxypropylene monoallyl ether.

Another example of component (a) is a (poly)oxyethylene derivative having carbon-carbon double bonds at the terminals of the molecular chain represented by the following structural formulae (4-1') to (4-4'). In the formulae, $X^1$, $X^2$, and $R^{10}$ are groups synonymous with the groups described above, and m and q are numbers synonymous with the numbers described above. R' is an unsaturated organic group having a carbon-carbon double bond at the terminal, and is preferably a substituted or unsubstituted, straight or branched unsaturated hydrocarbon group having from 3 to 5 carbon atoms. Examples of the unsaturated hydrocarbon group having from 3 to 5 carbon atoms include allyl groups, butenyl groups, methallyl groups, and similar alkenyl groups; and the unsaturated hydrocarbon group is preferably an allyl group.

[Formula 34]

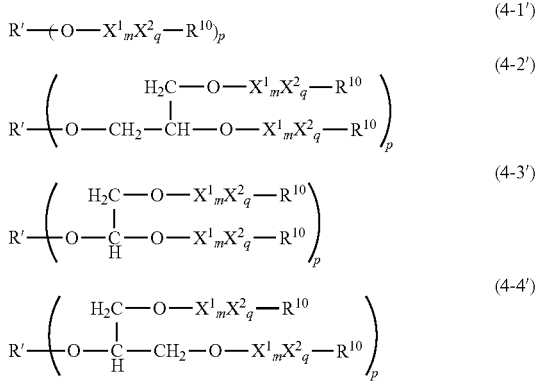

The (d) siloxane dendron compound having one reactive unsaturated group per molecule used in the synthesis of the (poly)oxyethylene group-containing organomodified silicone is preferably a compound having a siloxane dendron structure with one carbon-carbon double bond at a molecular terminal and is expressed by the following general formula (3'):

[Formula 35]

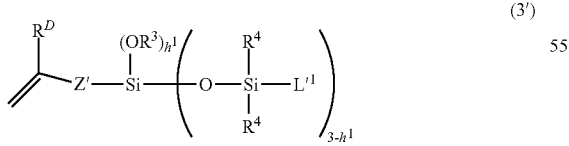

wherein
$R^3$ and $R^4$ are synonymous with those described above, $R^D$ is a hydrogen atom or a methyl group;
Z' is a divalent organic group;
$h^1$ is a number in a range of 0 to 3;
$L^{i1}$ is the $R^4$ moiety or, when j=1, a silylalkyl group expressed by general formula (3") below:

[Formula 36]

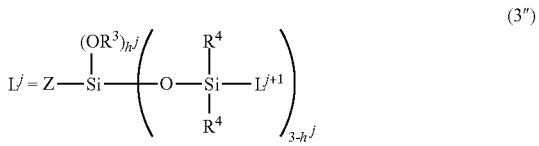

(wherein $R^3$ and $R^4$ are synonymous with those described above;
Z is a divalent organic group;
j indicates the number of generations of the silylalkyl group that is represented by $L^j$, when the number of generations (the number of repetitions) of the silylalkyl group is k', j is an integer of 1 to k', and the number of generations k' is an integer from 1 to 9; $L^{j+1}$ is the silylalkyl group when j is less than k' and is the $R^4$ moiety when j=k'; and
$h^j$ is a number in a range of 0 to 3).

The (e) hydrocarbon compound having one reactive unsaturated group per molecule or chain organopolysiloxane having one reactive unsaturated group per molecule used in the synthesis of the (poly)oxyethylene group-containing organomodified silicone is preferably a mono-unsaturated organic compound expressed by the following general formula (2'):

[Formula 37]

(wherein R' is synonymous with that described above; and
$R^{2'}$ represents a substituted or unsubstituted, straight or branched monovalent hydrocarbon group having from 7 to 58 carbon atoms) or the following general formula (2-1):

[Formula 38]

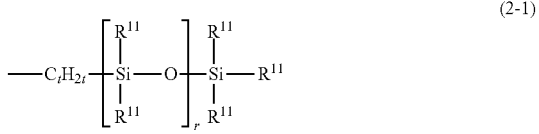

(wherein $R^{11}$, t, and r are synonymous with those described above); or the following general formula (2-2):

[Formula 39]

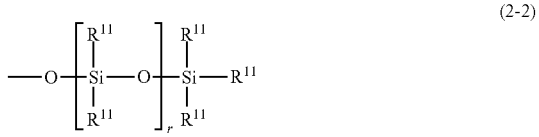

(wherein $R^{11}$ and r are synonymous with those described above).

The hydrocarbon compound having one reactive unsaturated group in the molecule (e) is preferably a monounsaturated hydrocarbons having from 9 to 30 carbon atoms and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

The hydrosilylation reaction used to synthesize the (poly) oxyethylene group-containing organomodified silicone or a composition containing the same can be carried out using a publicly known method in the presence or absence of a solvent. Here, examples of the reaction solvent include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride.

The hydrosilylation reaction may be performed in the presence or absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. If a platinum catalyst is used, the usage quantity of the solvent is approximately 0.0001 to 0.1 wt. %, and preferably 0.0005 to 0.05 wt. %, relative to the weight of the metal catalyst, but is not particularly limited.

A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio [amount of substance of carbon-carbon double bonds in (poly)oxyethylene group-containing compound/amount of substance of silicon-bonded hydrogen atoms to be added to the carbon-carbon double bonds of the (poly)oxyethylene group-containing compound in the organohydrogenpolysiloxane] is preferably in a range of 0.8 to 1.5, and more preferably in a range of 1.0 to 1.3. That is, when synthesizing the (poly)oxyethylene group-containing organomodified silicone or a composition containing a (poly)oxyethylene group-containing organomodified silicone, it is more preferable to use a slightly excessive amount of a (poly)oxyethylene group-containing compound. Although processing with the ratio above 1.5 is also possible, the proportion of residual raw material increases, so it is not economical. In addition, during the hydrosilylation reaction, the terminal carbon-carbon double bonds in the (poly)oxyethylene group-containing compound transition internally so that a deactivating side-reaction occurs simultaneously. Therefore, when the ratio described above is from 0.8 to 1.0, the silicon-bonded hydrogen atoms consumed by the hydrosilylation reaction settle to within a slightly lower range than the range of theoretical values from 0.8 to 1.0, so silicon-bonded hydrogen atoms remain at a slightly greater ratio than 0 to 0.2. However, it is also possible to cause dehydrogenation reactions with hydroxyl groups contained in the (poly)oxyethylene group-containing organic group and alcoholic hydroxyl groups of the reaction solvent, which can consume the remaining silicon-bonded hydrogen atoms, depending on the reaction conditions.

On the other hand, if the ratio is less than 0.8, there is a risk that unreacted organohydrogenpolysiloxane will remain. When such a (poly)oxyethylene group-containing organomodified silicone or a composition containing a (poly)oxyethylene group-containing organomodified silicone is used as a starting material for an external preparation or a cosmetic, residual organohydrogenpolysiloxane or a Si—H group may react with the other starting materials and generate hydrogen gas. This may cause such undesirable effects as alteration of the external preparation or the cosmetic into which the composition is introduced, fire, container expansion, and the like. In addition, when an attempt is made to consume the remaining silicon-bonded hydrogen atoms by using a dehydrogenation reaction when the ratio is less than 0.8, the proportion of Si—O—C crosslinked bonds increases, which increases the tendency to cause gelation during production. Therefore, to enable the complete and safe consumption of organohydrogenpolysiloxane, it is preferable for the ratio to exceed 0.8; that is, for 0.8 equivalents or more of the (poly)oxyethylene group-containing compound to be reacted.

(Organomodified Silicone having Si—C Bond in Crosslinking Part)

The organosilicon compound described above may be a liquid organomodified silicone having a silicon-bonded (poly)oxyethylene group-containing organic group and having a crosslinked structure containing a carbon-silicon bond in a crosslinking part.

The organomodified silicone can be obtained by reacting:
(A) an organohydrogenpolysiloxane;
(B) a (poly)oxyethylene group-containing organic compound having one or more reactive unsaturated groups in each molecule; and
(C) one or more types of organic compounds selected from a group consisting of (C1) an organic compound having a number of reactive unsaturated groups greater than 1 on average in each molecule and (C2) an organic compound having one or more reactive unsaturated groups and one or more epoxy groups in each molecule (however, the use of the component (B) is optional when the component (C) contains a (poly)oxyethylene group).

The (A) organohydrogenpolysiloxane is not particularly limited as long as it has silicon-bonded hydrogen atoms, but an organohydrogenpolysiloxane having more than one—preferably from 1.01 to 100, more preferably from 1.1 to 50, even more preferably from 1.2 to 25, and particularly preferably from 1.3 to 10—silicon-bonded hydrogen atoms in the molecule on average is preferable, and a straight-chain, branched, or reticulated organopolysiloxane may be used. The positions of the silicon-bonded hydrogen atoms in the organohydrogenpolysiloxane is not limited, and can be on the main chain or at the terminals. One type or two or more types of organohydrogenpolysiloxanes may be used as the component (A).

Examples of the component (A) include 1,1,3,3-tetramethyldisiloxane, 1,3,5,7-tetramethylcyclotetrasiloxane, methylhydrogenpolysiloxane capped at both molecular terminals with trimethylsiloxy groups, dimethylsiloxane-methylhydrogensiloxane copolymers capped at both molecular terminals with trimethylsiloxy groups, dimethylsiloxane capped at both molecular terminals with dimethylhydrogensiloxy groups, dimethylpolysiloxane capped at both molecular terminals with dimethylhydrogensiloxy groups, dimethylsiloxane-methylhydrogensiloxane copolymers capped at both molecular terminals with dimethylhydrogensiloxy groups, methylhydrogensiloxane-diphenylsiloxane copolymers capped at both molecular terminals with trimethylsiloxy groups, methylhydrogensiloxane-diphenylsiloxane-dimethylsiloxane copolymers capped at both molecular terminals with trimethylsiloxy groups, copolymers comprising $(CH_3)_2HSiO_{1/2}$ units and $SiO_{4/2}$ units, and copolymers comprising $(CH_3)_2HSiO_{1/2}$ units, $SiO_{4/2}$ units, and $(C_6H_5)SiO_{3/2}$ units.

The component (A) is preferably expressed by the average composition formula (1):

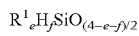  (1)

$$R^1_e H_f SiO_{(4-e-f)/2}$$

(wherein the $R^1$ moieties are each independently monovalent organic groups, $1.0 \leq 3 \leq 3.0$, and $0.001 \leq f \leq 1.5$).

Although the molecular structure of the (A) organohydrogenpolysiloxane is not limited, examples include straight-chain, partially branching straight-chain, branched-chain, cyclic, and dendric structures, and straight-chain is preferable. The molecular weight is not particularly limited, and products having a low molecular weight to products having a high molecular weight can be used. Specifically, the number-average molecular weight is preferably in a range of 100 to 1,000,000 and more preferably in a range of 300 to 500,000.

Examples of such organohydrogenpolysiloxanes includes those expressed by the following structural formulas:

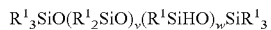  (i)

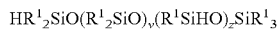  (ii)

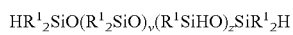  (iii)

(wherein $R^1$ is as described above, v is 0 or a positive integer, w is a positive integer, and z is 0 or a positive integer). These organohydrogenpolysiloxanes are straight-chain organohydrogenpolysiloxanes having a silicon-bonded hydrogen atom on (i) only the side chain, (ii) the side chain or one molecular terminal, or (iii) the side chain or both molecular terminals.

The monovalent organic group is not particularly limited but is preferably selected from the following (D1) to (D10):

(D1) a substituted or unsubstituted, straight-chain or branched monovalent hydrocarbon group having from 1 to 60 carbon atoms;

(D2) a polyoxyalkylene group expressed by $-R^8O(AO)_zR^9$ (wherein AO is an oxyalkylene group having from 2 to 4 carbon atoms; $R^8$ is a substituted or unsubstituted, straight-chain or branched divalent hydrocarbon group having from 3 to 5 carbon atoms; $R^9$ is a hydrogen atom, a substituted or unsubstituted, straight-chain or branched monovalent hydrocarbon group having from 1 to 24 carbon atoms, or a substituted or unsubstituted, straight-chain or branched acyl group having from 2 to 24 carbon atoms; and z=1 to 100);

(D3) a substituted or unsubstituted, straight-chain or branched alkoxy group having from 1 to 30 carbon atoms;

(D4) a hydroxyl group;

(D5) an ester group expressed by $-R^{10}-COOR^{11}$ (wherein $R^{10}$ is a substituted or unsubstituted, straight-chain or branched divalent hydrocarbon group having from 2 to 20 carbon atoms, and $R^{11}$ is a substituted or unsubstituted, straight-chain or branched monovalent hydrocarbon group having from 1 to 30 carbon atoms);

(D6) an ester group expressed by $-R^{17}-OCOR^{18}$ (wherein $R^{17}$ substituted or unsubstituted, straight-chain or branched divalent hydrocarbon group having from 2 to 20 carbon atoms, and $R^{18}$ is a substituted or unsubstituted, straight-chain or branched monovalent hydrocarbon group having from 1 to 30 carbon atoms);

(D7) $L^1$ here, $L^1$ is a silylalkyl group having a siloxane dendron structure and, when i=1, is expressed by the following general formula (3):

[Formula 40]

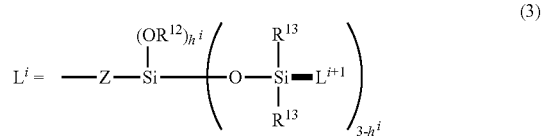  (3)

(wherein $R^{12}$ is a substituted or unsubstituted, straight-chain or branched monovalent hydrocarbon group having from 1 to 30 carbon atoms;

$R^{13}$ moieties each independently represents an alkyl group or a phenyl group having from 1 to 6 carbon atoms;

Z is a divalent organic group;

i represents a generation of the aforementioned silylalkyl group represented by $L^i$ and is an integer of 1 to k when k is the number of generations, which is the number of repetitions of the silylalkyl group; the number of generations k is an integer from 1 to 10; $L^{i+1}$ is the silylalkyl group when i is less than k, and $R^{13}$ when i=k; and $h^i$ is a number in a range of 0 to 3);

(D8) an alkyl group substituted by a chain polysiloxane structure expressed by the following general formula (4):

[Formula 41]

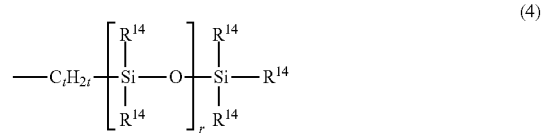  (4)

(wherein $R^{14}$ moieties are each independently substituted or unsubstituted, straight-chain or branched monovalent hydrocarbon groups having from 1 to 30 carbon atoms, hydroxyl groups, or hydrogen atoms, and at least one of the $R^{14}$ moieties is the monovalent hydrocarbon group; t is a number in a range of 2 to 10; and r is a number in a range of 1 to 100);

(D9) an epoxy group expressed by the following general formula (5):

[Formula 42]

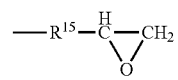  (5)

(wherein $R^{15}$ is a substituted or unsubstituted, straight-chain or branched divalent hydrocarbon group having from 2 to 20 carbon atoms); and (D10) a cycloaliphatic epoxy group expressed by the following general formula (6):

[Formula 43]

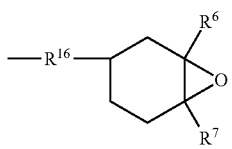

(6)

(wherein $R^{16}$ is a substituted or unsubstituted, straight-chain or branched divalent hydrocarbon group having from 2 to 20 carbon atoms, and $R^6$ and $R^7$ are each independently a substituted or unsubstituted, straight-chain or branched monovalent hydrocarbon group having from 1 to 30 carbon atoms).

Examples of the substituted or unsubstituted, straight-chain or branched monovalent hydrocarbon group in (D1), (D2), (D5) to (D8), and (D10) include alkyl groups such as methyl groups, ethyl groups, propyl groups, butyl groups, pentyl groups, hexyl groups, heptyl groups, and octyl groups; cycloalkyl groups such as cyclopentyl groups and cyclohexyl groups; alkenyl groups such as vinyl groups, allyl groups, and butenyl groups; aryl groups such as phenyl groups and tolyl groups; aralkyl groups such as benzyl groups; and groups in which the hydrogen atoms bonded to the carbon atoms of these groups are substituted at least partially by halogen atoms such as fluorine atoms or organic groups such as epoxy groups, glycidyl groups, acyl groups, carboxyl groups, amino groups, methacryl groups, and mercapto groups. The monovalent hydrocarbon group is preferably a group other than an alkenyl group, and is particularly preferably a methyl group, an ethyl group, or a phenyl group.

Examples of the substituted or unsubstituted, straight-chain or branched divalent hydrocarbon groups in (D2), (D5), (D6), (D9), and (D10) are as follows. Examples of the substituted or unsubstituted, straight-chain or branched divalent hydrocarbon group having from 1 to 30 carbon atoms include: straight-chain or branched alkylene groups having from 1 to 30 carbon atoms such as the methylene group, dimethylene group, trimethylene group, tetramethylene group, pentamethylene group, hexamethylene group, heptamethylene group, octamethylene group, or the like; alkenylene groups having from 2 to 30 carbon atoms such as the vinylene group, allylene group, butenylene group, hexenylene group, octenylene group, or the like; arylene groups having from 6 to 30 carbon atoms such as the phenylene group, diphenylene group, or the like; alkylenearylene groups having from 7 to 30 carbon atoms such as the dimethylenephenylene group or the like; and substituted groups thereof in which hydrogen atoms bonded to carbon atoms of the groups are at least partially substituted by a halogen atom such as a fluorine atom or the like, or an organic group containing the carbinol group, epoxy group, glycidyl group, acyl group, carboxyl group, amino group, methacryl group, mercapto group, amide group, oxyalkylene group, or the like. The divalent hydrocarbon groups are preferably alkylene groups having from 1 to 30 carbon atoms, more preferably are alkylene groups having from 1 to 6 carbon atoms, and even more preferably alkylene groups having from 3 to 5 carbon atoms.

Examples of the substituted or unsubstituted, straight-chain or branched alkoxy group in (D3) include lower alkoxy groups such as methoxy groups, ethoxy groups, isopropoxy groups, and butoxy groups and higher alkoxy groups such as lauryl alkoxy groups, myristyl alkoxy groups, palmityl alkoxy groups, oleyl alkoxy groups, stearyl alkoxy groups, and behenyl alkoxy groups.

Among the phenyl group or the alkyl group having from 1 to 6 carbon atoms of (D7), examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight, branched, or cyclic alkyl groups.

In the aforementioned general formula (3), in the case of i=k, $R^4$ is preferably a methyl group or a phenyl group. In particular, R4 is preferably a methyl group when i=k.

From an industrial standpoint, the number of generations k is preferably an integer from 1 to 3, and more preferably is 1 or 2. In each of the number of generations, the group represented by $L^1$ is expressed as follows. In these formulae, $R^{12}$, $R^{13}$, and Z are groups synonymous with the groups described above.

When the number of generations is k=1, $L^1$ is expressed by the following general formula (3-1).

[Formula 44]

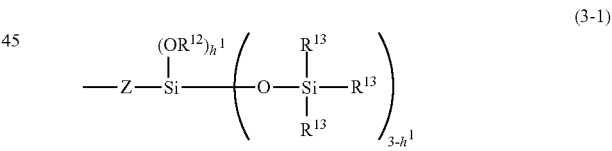

(3-1)

When the number of generations is k=2, $L^1$ is expressed by the following general formula (3-2).

[Formula 45]

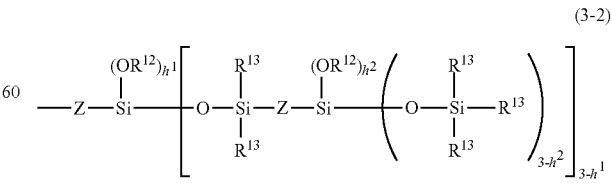

(3-2)

When the number of generations is k=3, $L^1$ is expressed by the following general formula (3-3).

[Formula 46]

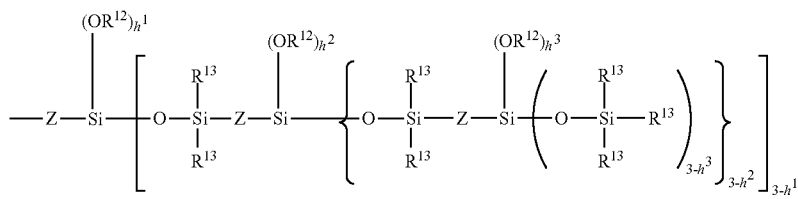

(3-3)

In the structures expressed by the general formulae (3-1) to (3-3) in the case of the number of generations is from 1 to 3, each of $h^1$, $h^2$ and $h^3$ moieties is independently a number in a range of 0 to 3. These $h^i$ moieties are preferably a number in a range of 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups expressed by the following general formula.

[Formula 47]

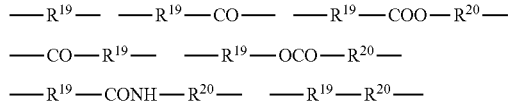

Of these, Z in $L^1$ is preferably a divalent organic group expressed by general formula —$R^{19}$— that is introduced by a reaction between a silicon-bonded hydrogen atom and an alkenyl group. Likewise, Z is preferably a divalent organic group expressed by general formula —$R^{19}$—COO—$R^{20}$— that is introduced by a reaction between a silicon-bonded hydrogen atom and an unsaturated carboxylic ester group. On the other hand, in the silylalkyl group represented by $L^i$, in which the number of generations k is 2 or more, and $L^i$ is $L^2$ to $L^k$, Z is preferably an alkylene group having from 2 to 10 carbon atoms or a divalent organic group represented by —$R^{19}$—COO—$R^{20}$— and is particularly preferably a group selected from an ethylene group, a propylene group, a methylethylene group, a hexylene group, and —$CH_2C(CH_3)COO-C_3H_6$—.

In the general formula described above, $R^{19}$ moieties are each independently a substituted or unsubstituted, straight or branched chain alkylene group or alkenylene group having from 2 to 22 carbon atoms or an arylene group having from 6 to 22 carbon atoms. More specifically, examples of $R^{19}$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^{20}$ is preferably a group selected from an ethylene group, a propylene group, a methylethylene group, and a hexylene group.

In the general formula described above, $R^{20}$ is a group selected from divalent organic groups expressed by the following formula.

[Formula 48]

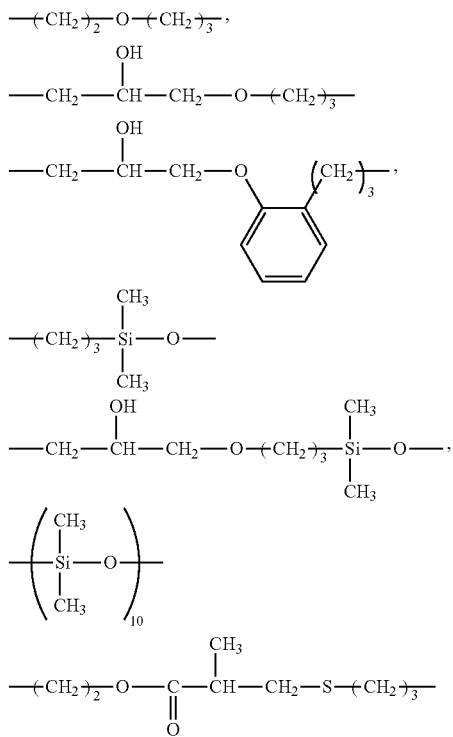

The (poly)oxyethylene group-containing compound (B) having a reactive unsaturated group is not particularly limited as long as it has at least one reactive unsaturated group and at least one (poly)oxyethylene modified group in each molecule, but the compound is preferably a (poly)oxyethylene derivative having carbon-carbon double bonds at the terminals of the molecular chain. These are, for example, (poly)oxyethylene derivatives having a reactive functional group such as an alkenyl group at the molecular chain terminal, such as an allyl (poly)oxyethylene, and can be synthesized according to a known method. Component (B) is preferably a (poly)oxyethylene monoallyl ether, a (poly)oxyethylene (poly)oxypropylene monoallyl ether, a composition in which the terminal hydroxyl groups thereof are capped with a lower alkyl group such as a methyl group, an acetyl group, or the like, a (poly)oxyethylene diallyl ether, a (poly)oxyethylene (poly)oxypropylene diallyl ether, a (poly)oxyethylene dimethallyl ether, or a (poly)oxyethylene (poly)oxypropylene dimethallyl ether. Of these, a (poly)oxyethylene monoallyl ether, a (poly)oxyethylene (poly)oxypropylene monoallyl ether, or a composition in which the terminal hydroxyl groups thereof are capped with a methyl group or an acetyl group is particularly preferable.

There are no particularly restrictions regarding the structure of (C1) the organic compound having an average number of reactive unsaturated groups in the molecule that is greater than 1 serving as the component (C) as long as the compound has more than 1-preferably from 1.01 to 10, more preferably from 1.2 to 8, even more preferably from 1.5 to 6, and particularly preferably from 2.0 to 4.5 reactive unsaturated groups and preferably carbon-carbon double bonds on average in the molecule, straight-chain, branched, or reticulated organic compounds may be used. An organopolysiloxane or an unsaturated aliphatic hydrocarbon is preferable as an organic compound. There are also no restrictions regarding the position of the reactive unsaturated group on the organic compound and preferably the organopolysiloxane or the unsaturated aliphatic hydrocarbon, and the component may be positioned on the main chain or on a terminal. However, from the perspective of the ease of controlling the crosslinking density, it is preferable to use a compound of high purity having two unsaturated groups in the molecule, each of which is positioned at either terminal, for example.

A reactive unsaturated group is preferably present in an unsaturated aliphatic hydrocarbon group. The unsaturated aliphatic hydrocarbon group preferably has from 2 to 30 carbon atoms and more preferably has from 2 to 20 carbon atoms. Examples of the monovalent unsaturated aliphatic hydrocarbon group having from 2 to 30 carbon atoms include straight-chain or branched alkenyl groups such as vinyl groups, 1-propenyl groups, allyl groups, isopropenyl groups, 1-butenyl groups, 2-butenyl groups, pentenyl groups, and hexenyl groups; cycloalkenyl groups such as cyclopentenyl groups and cyclohexenyl groups; cycloalkenylalkyl groups such as cyclopentenylethyl groups, cyclohexenylethyl groups, and cyclohexenylpropyl groups; and alkynyl groups such as ethynyl groups and propargyl groups. Alkenyl groups are preferred, and the vinyl group and hexenyl group are particularly preferred.

When the component (C1) is an organopolysiloxane, the unsaturated aliphatic hydrocarbon group containing a reactive unsaturated group is preferably bonded to a silicon atom. In addition, when the component (C1) is an organopolysiloxane, the group bonding to silicon atoms other than the unsaturated aliphatic hydrocarbon may be a substituted or unsubstituted monovalent hydrocarbon group or a monovalent organic group having a reactive functional group.

Substituted or unsubstituted monovalent hydrocarbon groups are typically substituted or unsubstituted, straight or branched monovalent saturated hydrocarbon groups having from 1 to 30 carbon atoms, preferably from 1 to 10 carbon atoms, and more preferably from 1 to 4 carbon atoms, and substituted or unsubstituted monovalent aromatic hydrocarbon groups having from 6 to 30 carbon atoms, and more preferably from 6 to 12 carbon atoms. Moreover, component (C1) may contain, as a monovalent organic group, a hydroxyl group or an alkoxy group having from 1 to 12 carbon atoms, such as a methoxy group, an ethoxy group, a propoxy group or a butoxy group.

Examples of the monovalent saturated hydrocarbon group having from 1 to 30 carbon atoms include straight chain or branched chain alkyl groups such as methyl groups, ethyl groups, n-propyl groups, isopropyl groups, n-butyl groups, isobutyl groups, sec-butyl groups, tert-butyl groups, pentyl groups, hexyl groups, heptyl groups, octyl groups, nonyl groups, decyl groups, and the like; and cycloalkyl groups such as cyclopentyl groups, cyclohexyl groups, cycloheptyl groups, cyclooctyl groups, and the like.

Examples of the monovalent aromatic hydrocarbon group having from 6 to 30 carbon atoms include aryl groups such as phenyl groups, tolyl groups, xylyl groups, mesityl groups, and the like. Of these, a phenyl group is preferable. Note that, in the present specification, "aromatic hydrocarbon group" also includes groups in which an aromatic hydrocarbon and a saturated aliphatic hydrocarbon are conjugated in addition to groups formed only from an aromatic hydrocarbon. Examples of groups in which an aromatic hydrocarbon and a saturated hydrocarbon are conjugated include aralkyl groups such as benzyl groups, phenethyl groups, and the like.

Hydrogen atoms in the above-mentioned monovalent hydrocarbon groups may be substituted by one or more substituted groups, and said substituted groups may be selected from the group consisting of, for example, a halogen atom (a fluorine atom, a chlorine atom, a bromine atom, or an iodine atom), a hydroxyl group, an amide group, an ester group, a carboxyl group and an isocyanate group. A monovalent saturated or aromatic hydrocarbon group having at least one of the above-mentioned substituted groups is preferred. Specifically, it is possible to use a 3,3,3-trifluoropropyl group, a 3-chloropropyl group, a 3-hydroxypropyl group, a 3-(2-hydroxyethoxy)propyl group, a 3-carboxypropyl group, a 10-carboxydecyl group, a 3-isocyanatopropyl group and the like.

Examples of monovalent organic groups having reactive functional groups include monovalent saturated or aromatic hydrocarbon groups having reactive functional groups selected from the group consisting of, for example, hydroxyl groups, mercapto groups, epoxy groups, amino groups, amide groups, ester groups, carboxyl groups and isocyanate groups. One or a plurality of reactive functional groups may exist in the monovalent organic group. $R^1$ is preferably a monosaturated or aromatic hydrocarbon group having at least one of the reactive functional groups described above. Specific examples of the reactive functional group include 3-hydroxypropyl groups, 3-(2-hydroxyethoxy)propyl groups, 3-mercaptopropyl groups, 2,3-epoxypropyl groups, 3,4-epoxybutyl groups, 4,5-epoxypentyl groups, 2-glycidoxyethyl groups, 3-glycidoxypropyl groups, 4-glycidoxybutyl groups, 2-(3,4-epoxycyclohexyl) ethyl groups, 3-(3,4-epoxycyclohexyl)propyl groups, aminopropyl groups, N-methylaminopropyl groups, N-butylaminopropyl groups, N,N-dibutylaminopropyl groups, 3-(2-aminoethoxy)propyl groups, 3-(2-aminoethylamino)propyl groups, 3-carboxypropyl groups, 10-carboxydecyl groups, 3-isocyanate propyl groups, and the like.

A straight-chain or branched polysiloxane is preferable as the component (C1). A straight-chain component (C1) is preferably a polymer having a diorganosiloxane unit and a triorganosiloxane unit, examples of which include dimethylpolysiloxanes capped at both molecular terminals with dimethylvinylsiloxy groups, copolymers of dimethylsiloxane and methylphenylsiloxane capped at both molecular terminals with dimethylvinylsiloxy groups, copolymers of dimethylsiloxane and methylvinylsiloxane capped at both molecular terminals with dimethylvinylsiloxy groups, copolymers of dimethylsiloxane and methylvinylsiloxane capped at both molecular terminals with trimethylsiloxy groups, copolymers of dimethylsiloxane, methylvinylsiloxane and methylphenylsiloxane capped at both molecular terminals with trimethylsiloxy groups, copolymers of dimethylsiloxane and methylvinylsiloxane capped at both molecular terminals with silanol groups, polymers in which some of the methyl groups in these polymers are substituted by alkyl groups other than methyl groups, such as ethyl groups or propyl groups, or halogenated alkyl groups such as 3,3,3-trifluoropropyl groups, and mixtures of two or more of these polymers, with straight-chain diorganopolysiloxanes having unsaturated aliphatic hydrocarbon groups, and especially alkenyl groups, at both molecular terminals only being particularly preferred.

It is particularly preferable for a branched chain polysiloxane of component (C1) to be a polymer that contains a diorganosiloxane unit, an organosilsesquioxane unit and a triorganosiloxy unit. Silicon-bonded organic groups in these units are preferably monovalent hydrocarbon groups including alkyl groups such as methyl groups, ethyl groups and propyl groups; alkenyl groups such as vinyl groups, allyl groups, butenyl groups and hexenyl groups; aryl groups such as phenyl groups and tolyl groups; and halogenated alkyl groups such as 3,3,3-trifluoropropyl groups, and the like, and may contain extremely small quantities of hydroxyl groups and alkoxy groups such as methoxy groups, but at least two silicon-bonded organic groups in this polymer must be unsaturated aliphatic hydrocarbon groups, and especially alkenyl groups. In addition, the proportions of these units are not limited, but in this polymer, it is preferable for diorganosiloxane units to account for in the range of 80.00 to 99.65 mol % and organosilsesquioxane units to account for in the range of 0.10 to 10.00 mol %, with the balance comprising triorganosiloxy units.

Examples of the component (C1) include (C1-5) unsaturated group-containing silicone compounds expressed by the average composition formula (2-5):

$$R^5_p R^6_q SiO_{(4-p-q)/2} \tag{2-5}$$

(wherein $R^5$ moieties may each be independent from one another but are monovalent organic groups that are different from $R^6$;

$R^6$ moieties are each independently monovalent unsaturated aliphatic hydrocarbon groups having from 2 to 30 carbon atoms, $1 \le p \le 2.5$, and $0.001 \le q \le 1.5$). The monovalent unsaturated aliphatic hydrocarbon group having from 2 to 30 carbon atoms is as described above.

In the average composition formula (2-5), the monovalent organic group represented by $R^5$ is not particularly limited, but is preferably selected from the following (E1) to (E6):

(E1) a substituted or unsubstituted, straight-chain or branched monovalent hydrocarbon group having from 1 to 60 carbon atoms (excluding monovalent hydrocarbon groups having from 2 to 20 carbon atoms and an aliphatic unsaturated group);
(E2) a hydroxyl group;
(E3) an ester group expressed by —$R^{10}$—$COOR^{11}$ (wherein $R^{10}$ and $R^{11}$ are as defined above);
(E4) an ester group expressed by —$R^{17}$—$OCOR^{18}$ (wherein $R^{17}$ and $R^{18}$ are as defined above);
(E5) an amide group expressed by —$R^{21}$—$NR^{22}COR^{23}$ (wherein $R^{21}$ is a substituted or unsubstituted, straight-chain or branched divalent hydrocarbon group having from 2 to 20 carbon atoms, $R^{22}$ is a hydrogen atom, or a substituted or unsubstituted, straight-chain or branched monovalent hydrocarbon group having from 1 to 20 carbon atoms, and $R^{23}$ is a substituted or unsubstituted, straight-chain or branched monovalent hydrocarbon group having from 1 to 30 carbon atoms); and (E6) an amide group expressed by —$R^{24}$—$CONR^{25}R^{26}$ (wherein $R^{24}$ is a substituted or unsubstituted, straight-chain or branched divalent hydrocarbon group having from 2 to 20 carbon atoms, and $R^{25}$ and $R^{26}$ are each independently a hydrogen atom or a substituted or unsubstituted, straight-chain or branched monovalent hydrocarbon group having from 1 to 20 carbon atoms). The definitions, types, and the like of the substituted or unsubstituted, straight-chain or branched monovalent hydrocarbon groups or divalent hydrocarbon groups are as described above.

On the other hand, the component (C1) may be an unsaturated aliphatic hydrocarbon. Examples of unsaturated aliphatic hydrocarbons include various dienes, diynes, enynes, and similar products having two or more reactive unsaturated groups. In view of crosslinking, dienes, diynes, and enynes are preferable. Dienes, diynes, and enynes are compounds having a structure in which at least two reactive unsaturated groups are separated by one or more, and preferably two or more single bonds in a molecule. The unsaturated aliphatic hydrocarbon group may be present at the terminal of the molecular chain, or as a pendant group in the molecular chain.

Examples of unsaturated aliphatic hydrocarbons serving as the component (C1) include α,ω-unsaturated alkenes and alkynes having from 2 to 30 carbon atoms. Examples of the component (C1) include an α,ω-diene expressed by the general formula (2-1):

$$CH_2=CH(CH_2)_xCH=CH_2 \tag{2-1}$$

(wherein $1 \le x \le 20$); an α,ω-diyne expressed by the general formula (2-2):

$$CH \equiv C(CH_2)_xC \equiv CH \tag{2-2}$$

(wherein $1 \le x \le 20$); and an α,ω-ene-yne expressed by the general formula (2-3):

$$CH_2=CH(CH_2)_xC \equiv CH \tag{2-3}$$

(wherein $1 \le x \le 20$).

Specific examples of unsaturated aliphatic hydrocarbons serving as the component (C1) include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, 1,19-eicosadiene, 1,3-butadiene, 1,5-hexadiyne, and 1-hexene-5-yne.

The component (C1) may be a single component, but may also be a mixture of two or more components having different structures. That is, the component (C1) may be a mixture of one or more types of organopolysiloxanes and one or more types of unsaturated aliphatic hydrocarbons. Therefore, "having a number of reactive unsaturated groups greater than 1 on average" means having more than one reactive unsaturated group per molecule when two or more types of organopolysiloxanes and/or unsaturated aliphatic hydrocarbons are used.

The (C2) organic compound having at least one reactive unsaturated group and at least one epoxy group in the molecule serving as the component (C) is not structurally limited as long as the compound has a total of two or more—preferably from 2 to 10, more preferably from 2 to 7, even more preferably from 2 to 5, and particularly preferably from 2 to 4 —reactive unsaturated groups and epoxy groups in the molecule, and straight-chain, branched, or reticulated organic compounds can be used. An organopolysiloxane or an unsaturated aliphatic hydrocarbon is preferable as an organic compound. There are also no restrictions regarding the position of the reactive unsaturated group on the organic compound and preferably the organopolysiloxane or the unsaturated aliphatic hydrocarbon, and the component may be positioned on the main chain or on a terminal. However, from the perspective of the ease of controlling the crosslinking density, it is preferable to use a compound of high purity in which the total of unsaturated groups and epoxy groups in the molecule is two.

A reactive unsaturated group is preferably present in an unsaturated aliphatic hydrocarbon group. Examples of unsaturated aliphatic hydrocarbon groups are as described above.

When the component (C2) is an organopolysiloxane, the unsaturated aliphatic hydrocarbon group containing a reactive unsaturated group and/or the epoxy group-containing organic group is preferably bonded to a silicon atom. In addition, when the component (C2) is an organopolysiloxane, the group bonding to silicon atoms other than the unsaturated aliphatic hydrocarbon or the epoxy group-containing organic group may be a substituted or unsubstituted monovalent hydrocarbon group or a monovalent organic group having a reactive functional group as described above.

The component (C2) is preferably an epoxy group-containing unsaturated aliphatic hydrocarbon having at least one epoxy group. Examples of the unsaturated aliphatic hydrocarbon include compounds having the unsaturated aliphatic hydrocarbon groups described above. A compound having a monovalent unsaturated aliphatic hydrocarbon group is preferable.

Examples of the component (C2) include an unsaturated epoxy compound expressed by the general formula (2-6):

[Formula 49]

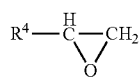

(2-6)

(wherein R$^4$ has one reactive unsaturated group and is a substituted or unsubstituted, straight-chain or branched monovalent hydrocarbon group having from 2 to 20 carbon atoms); and an unsaturated group-containing alicyclic epoxy compound represented by the general formula (2-7):

[Formula 50]

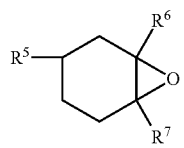

(2-7)

(wherein R$^5$ has one reactive unsaturated group and is a substituted or unsubstituted, straight-chain or branched monovalent hydrocarbon group having from 2 to 20 carbon atoms; and
R$^6$ and R$^7$ area each independently a substituted or unsubstituted, straight-chain or branched monovalent hydrocarbon group having from 1 to 30 carbon atoms). The definitions, types, and the like of the reactive unsaturated groups in the general formulas above and the substituted or unsubstituted, straight-chain or branched monovalent hydrocarbon groups are as described above.

Specific epoxy group-containing unsaturated aliphatic hydrocarbons serving as the component (C2) include an allylglycidylether, methallylglycidylether, 1-methyl-4-isopropenylcyclohexene oxide, 1,4-dimethylcyclohexene oxide, 4-vinylcyclohexene oxide, vinylnorbornene monooxide, dicyclopentadiene monooxide, butadiene monooxide, 1,2-epoxy-5-hexene, 1,2-epoxy-9-decene, and 2,6-dimethyl-2,3-epoxy-7-octene. Among these, 4-vinyl cyclohexane oxide is preferable.

The component (C2) may be a single component, but may also be a mixture of two or more components having different structures.

The reaction for producing the organomodified silicone described above can be performed in accordance with a publicly known method in the presence or absence of a reaction solvent. The reaction between the unsaturated group and the Si—H group in the present invention is a hydrosilylation reaction. In addition, when crosslinking is performed using an epoxide of (C2) the organic compound having one or more reactive unsaturated groups and one or more epoxy groups in the molecule, bonding caused by the reaction of the unsaturated group and the Si—H group and ether bond generation caused by the self ring-opening polymerization of the epoxy groups (cationic polymerization reaction that occurs in the presence of a SiH group and a platinum catalyst) both occur, resulting in crosslinking. In order to accelerate this reaction, irradiation using high energy beams such as ultraviolet light can be applied, or a common cation polymerization catalyst can be further added.

The reaction solvent is not particularly limited as long as the solvent is non-reactive, and examples thereof include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride. An oil agent described below may also be used as a reaction solvent. When an oil agent is used as a reaction solvent, it is possible to directly obtain a composition containing an oil agent and a liquid organomodified silicone having a silicon-bonded (poly)oxyethylene group-containing organic group and having a crosslinked structure containing a carbon-silicon bond in a crosslinking part after the crosslinking reaction.

The hydrosilylation reaction may be performed in the presence or absence of a catalyst, but preferably is performed in the presence of a catalyst because the reaction can be carried out at a low temperature and in a shorter period of time. Examples of the hydrosilylation reaction catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. A usage amount of the catalyst is about 0.5 to 1000 ppm in terms of platinum metal, when using a platinum catalyst.

A reaction temperature of the hydrosilylation reaction is typically from 30 to 150° C., and a reaction time is typically from 10 minutes to 24 hours and preferably from 1 to 10 hours.

The component (A) is crosslinked by the component (C) as a result of the hydrosilylation reaction or the cationic polymerization reaction of the epoxy groups, and the polysiloxane chains originating from the component (A) are linked by the crosslinking portion having a carbon-silicon bond originating from the component (C). In addition, component (A) is provided with a (poly)oxyethylene modified group originating from component (B). In this way, it is possible to obtain the liquid organomodified silicone of the present invention having a silicon-bonded (poly)oxyethylene group-containing organic group and having a crosslinked structure containing a carbon-silicon bond in a crosslinking part.

Further, the liquid organomodified silicone of the present invention having a silicon-bonded (poly)oxyethylene group-containing organic group and having a crosslinked structure containing a carbon-silicon bond in a crosslinking part essentially has a linked structure formed by the crosslinking part containing a carbon-silicon bond originating from the component (C), but it may also have a portion crosslinked by the Si—O—C bond. This is because when the structure has a condensation-reactable functional group such as a silanol group or an alkoxy group in the components (A) to (C), links can not only be formed between polysiloxane chains but can also be formed intermittently as a result of a partial reaction between the hydroxyl groups in the (poly)oxyethylene group-containing organic group originating from the component (B) and the Si—H groups of (A) when the crosslinking conditions are severe.

In the production of the liquid organomodified silicone of the present invention having a silicon-bonded (poly)oxyethylene group-containing organic group and having a crosslinked structure containing a carbon-silicon bond in a crosslinking part, the component (C) may be further reacted with the component (A) after a reaction between the component (A) and the component (B), or the component (B) may be further reacted with the component (A) after a reaction between the component (A) and the component (C).

When the component (C) is further reacted with the component (A) after the reaction between the component (A) and the component (B), the average value of the number of silicon-bonded hydrogen atoms per molecule of the component (A) reacting with the reactive unsaturated groups of the component (C) is preferably at least 1.0. That is, the number of silicon-bonded hydrogen atoms per molecule of the component (A) which constitute the crosslinking portion and react with the reactive unsaturated groups in the component (C) is, on average, at least 1.0, preferably within a range of 0.2 to 1.5, and particularly preferably within a range of 0.6 to 1.3.

(Organomodified Silicone Containing Si—O—C Bond in Crosslinking Part)

The organosilicon compound may be an organomodified silicone having a crosslinked structure containing a Si—O—C chain in the crosslinking part, and the (poly)oxyethylene group-containing organic block constituting the crosslinking part has at least two carbon atom bonds in the organic block and binds to a siloxane block with a chain, while the siloxane block consists of siloxane units in which 1 to 3 monovalent organic groups bind to silicon atoms, and the siloxane block has at least two silicon atom bonds. Such an organomodified silicone containing a Si—O—C bond in the crosslinking part is disclosed, for example, in U.S. Pat. No. 3,867,420.

The siloxane block is represented by the following general formula (5):

$$R^{13}{}_g R^{14}{}_s SiO_{(4-g-s)/2} \tag{5}$$

(wherein
the $R^{13}$ moieties may be independent of one another but differ from $R^{14}$ and are each a monovalent organic group bonded to the silicon atoms of general formula (5) by Si—C bonds; the $R^{14}$ moieties are oxygen atoms which bond to the silicon atoms and are linked to the carbon atoms of a (poly)oxyethylene group-containing organic block; $1.0 \leq g \leq 3.0$; $0 \leq s \leq 2.0$; and $1.0 \leq g+s \leq 3.0$); the (poly)oxyethylene group-containing organic block constituting the crosslinking part is represented by the following general formula (6):

[Formula 51]

(6)

(wherein Y is a polyvalent organic group having a valency of y1+y2; $R^{15}$ is a group selected from a group consisting of a hydrogen atom, $R^{13}$NHCO—, $R^{13}$CO—, and $R^{13}$; $2 \leq n \leq 4$; y is the total value of the number of repetitions of oxyethylene units, oxypropylene units, and oxybutylene units; $1 \leq y \leq 180$; $2 \leq y1$; $0 \leq y2 \leq 14$; and $2 \leq y1+y2 \leq 14$); and the (poly)oxyethylene group-containing organic block other than the (poly)oxyethylene group-containing organic block constituting the crosslinking part is represented by the following general formula (7):

[Formula 52]

(7)

(wherein X is a polyvalent organic group having a valency of y3+1; $R^{15}$, n, and y are synonymous with those described above; and $1 \leq y3$).

The groups described above can be used as the monovalent organic group. In addition, the polyvalent organic group is not particularly limited, but the groups described above as divalent organic groups, for example, can be used.

(Organomodified Silane)

The organomodified silane may be an organomodified silane represented by the following general formula (8):

[Formula 53]

(8)

(wherein $R^{16}$ is a group selected from a hydrogen atom and substituted or unsubstituted, straight-chain or branched monovalent hydrocarbon groups having from 1 to 30 carbon atoms; $X^1$ is a hydrolyzable group selected from alkoxy groups, aryloxy groups, acyloxy groups, secondary amino groups, and aminoxy groups; $Z^1$ is a monovalent organic group differing from $R^{16}$ which is linked to the silicon atoms of general formula (8) by Si—C bonds; $1 \le k \le 3$; $0 \le j \le 2$; and $k+j \le 3$). $Z^1$ is preferably a (poly)oxyethylene group-containing organic group having a structure in which the (poly)oxyethylene site bonds with a silicon atom via a divalent organic group, and is particularly preferably a (poly)oxyethylene group-containing organic group represented by the formula: —$(C_2H_4O)_{t1}(C_3H_6O)_{t2}(C_4H_8O)_{t3}$—$R^{10}$ (wherein t1, t2, and t3 are numbers satisfying $1 \le t1 \le 100$, $0 \le t2 \le 100$, and $0 \le t3 \le 50$, preferably numbers satisfying $1 \le t1 \le 50$, $0 \le t2 \le 50$, and $0 \le t3 \le 30$, and more preferably numbers satisfying $1 \le t1 \le 30$, $0 \le t2 \le 30$, and $0 \le t3 \le 10$; and $R^{10}$ is a group selected from an alkyl group, an acyl group, and a glycidyl group having from 1 to 20 carbon atoms). The monovalent hydrocarbon group and monovalent organic group are as described above.

((Poly)oxyalkylene Group-containing Alternating Copolymer)

The organosilicon compound may be an organomodified silicone in the form of a straight-chain (poly)oxyalkylene group-containing alternating copolymer obtained by reacting at least:

(D) an organopolysiloxane having reactive functional groups at both terminals of a molecular chain; and (E) an organic compound having two reactive functional groups capable of reacting with the reactive functional groups positioned at both of the molecular chain terminals of the organopolysiloxane (D) in the molecule.

Here, the (poly)oxyalkylene group may be contained in the molecular structure of (D) or may be contained in the molecular structure of (E). In addition, it may be (F) a (poly)oxyalkylene group-containing compound having two reactive functional groups capable of reacting with the reactive functional groups positioned at both terminals of the molecular chain of (D) or (E), or it may be an organomodified silicone in the form of a straight-chain (poly)oxyalkylene group-containing alternating copolymer obtained by further reacting a composition differing from (D) and (E).

The composition of reactive functional groups described here is not particularly limited, but examples thereof include combinations of Si—H groups and C=C groups, combinations of amino groups and organic groups that are reactive with amino groups (epoxy groups, carboxylic acid groups, carbonyl groups, ester groups, aldehyde groups, isocyanate groups, acid anhydride groups, acid halide groups, and the like), and combinations of hydroxyl groups and organic groups that are reactive with hydroxyl groups (epoxy groups, carboxylic acid groups, ester groups, alkoxy groups, aldehyde groups, isocyanate groups, acid anhydride groups, acid halide groups, and the like).

Specific examples of the (poly)oxyalkylene group-containing alternating copolymer described above include the block copolymers described in Japanese Unexamined Patent Application Publication No. H05-310944, Japanese Unexamined Patent Application Publication No. H04-234307, and Japanese Unexamined Patent Application Publication No. H04-211605 of Nippon Unicar Co., Ltd. and the silicone polyether block copolymer described in Japanese Examined Patent Application Publication (Translation of PCT Application) No. 2010-523790 (WO/2008/127519) of the Dow-Corning Corporation. Similarly, other examples include the (poly)oxyalkylene group-containing alternating copolymers described in Japanese Unexamined Patent Application Publication No. S56-062824, Japanese Unexamined Patent Application Publication No. H01-249109, Japanese Unexamined Patent Application Publication No. H07-126392, Japanese Unexamined Patent Application Publication No. H08-073596, Japanese Unexamined Patent Application Publication No. H06-100676, Japanese Unexamined Patent Application Publication No. H10-279807, Japanese Examined Patent Application Publication (Translation of PCT Application) No. 2004-528412, Japanese Unexamined Patent Application Publication No. 2000-063523, Japanese Examined Patent Application Publication (Translation of PCT Application) No. 2005-535760, Japanese Unexamined Patent Application Publication No. 2004-331977, Japanese Unexamined Patent Application Publication No. 2005-344116, Japanese Examined Patent Application Publication (Translation of PCT Application) No. 2008-534721, Japanese Unexamined Patent Application Publication No. 2008-156637, and Japanese Unexamined Patent Application Publication No. 2008-156638.

In order to prevent oxidative degradation, the oxidative stability can be increased by adding phenols to the high-purity organosilicon compound obtained with the production method of the present invention. In the case of applications such as cosmetics and external preparations, adding BHT(2,6-di-t-butyl-p-cresol), vitamin E, or the like, for example, will result in a further increase in stability. In this case, an added amount of the antioxidant that is used is in a range (by weight (mass)) of 10 to 1,000 ppm, and preferably of 50 to 500 ppm, of the high-purity organosilicon compound.

(Production Method for Solution Containing High-purity Organosilicon Compound)

In the production method of the present invention, when the mixture of the organosilicon compound and impurities—in particular, impurities originating from the organic modifier—contains the solvent of the organosilicon compound, a solution containing a high-purity high-purity organosilicon compound can be produced.

Any solvent can be used as long as it satisfies the condition of being a fluid that is a good solvent for the organosilicon compound, but it preferably further satisfies the condition of being a fluid that is a good solvent for the organosilicon compound and a poor solvent for the impurities. For example, the solvent is one or more oil agents selected from various silicone oils and organomodified silicones in a liquid state at normal temperature to 100° C., organomodified silane compounds such as silane coupling agents, and non-polar organic compounds or lowly polar to highly polar organic compounds, and it may be volatile or nonvolatile. A silicone oil agent or a silane coupling agent is optimal as the solvent, but of non-polar organic compounds and lowly polar to highly polar organic compounds, hydrocarbon oils, fatty acid ester oils, and liquid fatty acid triglycerides are preferable. In addition, the solvent may be a mixed fluid of a silicone oil agent and an organic compound.

The timing of adding the solvent to the mixture containing the organosilicon compound as a main component and containing impurities—in particular, impurities originating from the organic modifier serving as a starting material of the organosilicon compound—may be before, after, or during the treatment with the organic wax. Further, the mixture may already contain the solvent at the stage when the mixture undergoes treatment with an acidic aqueous solution as described below (including before, after, and during treatment). A solution containing the high-purity organosilicon compound of the present invention can be produced in the same manner as in the production method for a high-purity organosilicon compound of the present invention described above in all other respects.

In order to prevent oxidative degradation, the antioxidants described above may be blended into the solution of the high-purity organosilicon compound obtained with the production method of the present invention. The compounding ratios of the antioxidants are also as described above.

(Acid Treatment and Odor Reduction of Mixture Containing Organosilicon Compound and Impurities)

In the production method of the present invention, when the mixture containing the organosilicon compound and impurities—in particular, impurities originating from the organic modifier—is treated with an acidic aqueous solution and water and odor-causing substances produced by treatment with the acidic aqueous solution are removed by heating or depressurization, it is possible to obtain an organosilicon compound of even higher purity.

The acidic substance contained in the acidic aqueous solution can be selected discretionally, but it is optimal to use one or more types of acidic inorganic salts which are solids at 25° C., are water-soluble, and have an aqueous solution pH of at most 4 at 25° C. when 50 g is dissolved in 1 L of ion-exchanged water. In addition, when treatment is performed using this acidic aqueous solution, it is preferably performed prior to the treatment for increasing purity using the organic wax, but it may also be performed after or at the same time as the treatment for increasing purity using the organic wax.

Further, treatment using the acidic aqueous solution can be most preferably performed when the organosilicon compound is an organomodified silicone synthesized by a hydrosilylation reaction. Organomodified silanes typically have a low molecular weight and have hydrolyzable groups containing Si—O—C bonds in the molecules, so performing treatment in the presence of an acidic solution containing water causes dealcohol condensation, which induces oligomerization and causes the composition to lose its monomolecular state. Therefore, from the perspective of increasing the purity of an organomodified silane, it is preferable to perform only the aforementioned purification-increasing treatment using an organic wax and not to perform acid treatment. However, a high-purity organomodified silane oligomer can be obtained by performing treatment with an acidic aqueous solution on a mixture containing an organomodified silane as a main component and containing components originating from the organic modifier serving as a starting material of the organomodified silane as impurities so as to produce an organomodified silane oligomer (that is, an organomodified silicone), and then performing the aforementioned purification-increasing treatment with the organic wax so as to remove the impurities originating from the organic modifier. The production method for a high-purity organomodified silicone using such a technique is also a method to which the technical principle of the present invention is applied.

On the other hand, when the organosilicon compound is an organomodified silicone in which organic modified groups are linked primarily by Si—O—C bonds, the organic modifier serving as a starting material of the organomodified silicone does not contain odor-causing reactive unsaturated groups, acetal compounds originating from reactive unsaturated groups, or the like. Therefore, the aforementioned treatment using an acidic aqueous solution is unnecessary.

Accordingly, the case of a (poly)oxyethylene-modified silicone synthesized by a hydrosilylation reaction will be described hereinafter as an example of an acid treatment and odor reducing method for an organosilicon compound and a mixture containing the same.

Acid treatment preferably includes:
a process (V) of synthesizing a (poly)oxyethylene-modified silicone or a reaction mixture containing the same as a main component by performing a hydrosilylation reaction on: (ax) a (poly)oxyethylene derivative having carbon-carbon double bonds at the terminals of the molecular chain; and
(bx) an organohydrogenpolysiloxane; and
together with the synthesis process (V) or after the synthesis process (V), a process (W) of treating a (poly)oxyethylene-modified silicone or a reaction mixture containing the same as a main component
in the presence of at least of acidic inorganic salts which are solids at 25° C., are water-soluble, and have an aqueous solution pH of at most 4 at 25° C. when 50 g is dissolved in 1 L of ion-exchanged water.

In addition, because a treatment process that uses the acidic inorganic salt involves the generation of odor-causing substances it is more preferable to include a process of removing odor-causing substances by heating or depressurizing after process (W), from the perspective of odor reduction effectiveness.

For example, in process (V), when the hydrosilylation reaction is performed using (ax) a (poly)oxyethylene derivative such as a (poly)oxyethylene monoallyl ether and (bx) a straight-chain organohydrogenpolysiloxane represented by the structural formula (1-1A) in amounts so that there is an excessive amount of the substance of the component (ax) with respect to the silicon-bonded hydrogen atoms in the component (bx), the (poly)oxyethylene-modified silicone represented by structural formula (1-1) is synthesized, and a crude product of the (poly)oxyethylene-modified silicone and a reaction mixture containing the unreacted component (ax) and containing the (poly)oxyethylene-modified silicone as a main component is obtained.

Process (W) is a process for efficiently reducing the odors of the composition highly effectively and effectively suppressing the generation of odors over time by hydrolyzing the crude product using specific acidic inorganic salts, with practically no breakage of the silicon-oxygen bonds forming the main chain of polysiloxane or the carbon-oxygen bonds of side chain portions.

Process (W) specifically removes odor-causing substances from the crude product of the reaction mixture containing the (poly)oxyethylene-modified silicone as a main component by using hydrolysis, and it is characterized by performing treatment in the presence of one or more types of acidic inorganic salts which are solids at 25° C., are water-soluble, and have an aqueous solution pH of at most 4 at 25° C. when 50 g is dissolved in 1 L of ion-exchanged water. Note that pH values in the present invention are values that are measured using a pH meter having a glass electrode in a sample aqueous solution at room temperature (25°). In the present application, HM-10P produced by DKK-TOA Corporation was used for the pH measurement.

The acidic inorganic salt serving as a component (cx) must be a solid at 25°, must be water-soluble, and the aqueous solution must have a pH of at most 4 when 50 g of the acidic inorganic salt is dissolved in 1 L of ion exchanged water. The pH is preferably at most 3.5 and particularly preferably at most 2.0. By using such a water-soluble acidic inorganic salt for hydrolysis treatment of the composition, it is possible to reduce odors in the composition highly effectively and suppress odorization over time effectively, with almost no breakage of C—O bonds or Si—O bonds.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the component (cx) is preferably at least one type of acidic inorganic salt comprising a hydrogensulfate ion ($HSO_4^-$) or a hydrogensulfite ion ($HSO_3^-$) and a monovalent cation ($M^+$). Examples of the monovalent cation (Mt) include alkali metal ions or an ammonium ion. Particularly, the monovalent cation is preferably at least one type selected from the group consisting of a sodium ion, a potassium ion, and an ammonium ion. Additionally, one type of the acidic inorganic salt may be used alone or two or more types of acidic inorganic salt may be used. Furthermore, the acidic inorganic salt can be easily removed via filtration because the acidic inorganic salt is solid at room temperature (25° C.). Additionally, because it is water soluble, the acidic inorganic salt can be easily rinsed off using water, even in the cleaning process after production.

On the other hand in hydrolysis treatment based on an acetic acid salt, phosphoric acid salt, and the like that does not satisfy the conditions of the component (cx), it is impossible to sufficiently reduce the odor of the composition after hydrolysis. On the other hand, in hydrolysis treatment based on a strong acid such as hydrochloric acid and the like, and in hydrolysis treatment based on a publicly known solid acid of zirconium sulfate and the like, the odor can be reduced by a certain amount, but C—O bonds and Si—O bonds of the composition break easily at the time of hydrolysis.

Specific examples of the acidic inorganic salt serving as the component (cx) are lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof. The pH of aqueous solutions in which 50 g of the acidic inorganic salt is dissolved in 1 L of ion exchanged water is as shown in Table below. From the perspective of the technical benefit of reducing odor, the water soluble acidic inorganic salt having a pH of not higher than 2.0 is most preferably at least one type of acidic inorganic salt selected from the group consisting of sodium hydrogensulfate, potassium hydrogensulfate, and ammonium hydrogensulfate.

TABLE 1

| Acidic inorganic salt | pH (50 g/L) |
|---|---|
| Sodium hydrogensulfate | 1.5 or lower |
| Potassium hydrogensulfate | 2.0 or lower |
| Ammonium hydrogensulfate | 1.5 or lower |
| Sodium hydrogensulfite | 3.5 |

For example, treatment in the presence of an acidic inorganic salt refers to (1) decomposition treatment involving adding and stifling the acidic inorganic salt into the reaction system (for example, a reaction vessel such as a flask) of the reaction mixture containing the (poly)oxyethylene-modified silicone synthesized by a hydrosilylation reaction as a main component, and (2) hydrolysis treatment or the like involving adding and stirring an acidic inorganic salt and water or an acidic inorganic salt, water, and a hydrophilic solvent. The treatment process that uses the acidic inorganic salt is preferably carried out in the presence of water and/or a hydrophilic solvent.

A particularly preferable hydrolysis treatment is a hydrolysis treatment whereby, after the aforementioned process (V), at least an acidic inorganic salt and water are added to a reaction system containing a crude product of the reaction mixture containing the (poly)oxyethylene-modified silicone as a main component, and depending on the case, another hydrophilic solvent is further added with the objective of increasing the treatment efficiency by improving compatibility, and the solution is further stirred using a mechanical force. The hydrolysis can be carried out at any temperature and treatment time, and can be carried out at a temperature from 0 to 200° C. and more preferably from 50 to 100° C. for a reaction time of from 0.1 to 24 hours and more preferably from about 0.5 to 10 hours. The amount of the acidic inorganic salt that is used can be selected appropriately in accordance with the treatment apparatus and the treatment time. However, the amount is preferably within a range of 50 to 10,000 ppm and more preferably within a range of 100 to 5,000 ppm with respect to the reaction mixture containing the (poly)oxyethylene-modified silicone as a main component.

After the acid treatment described above, it is preferable to include a stripping process in which low-boiling-point components (propionaldehyde and the like), which are odor-causing substances, are removed. In addition, after stripping, it is possible to hydrolyze more of the propenyl ether group-containing (poly)oxyethylene derivative or the like by treating again in the presence of an acidic inorganic salt, and propionaldehyde and the like, which are odor-causing substances, can be removed. At this time, there is an advantage that, because acidic inorganic salt remains, an acidic inorganic salt need not be newly added. Therefore, it is only necessary to add a hydrophilic solvent, typified by water. That is, the aforementioned process [W] and the stripping process can be repeated two times or more, to increase the degree of odor reduction, or the like.

Furthermore, the "materials with a low boiling point" which are distilled off by the stripping process, include not only propionaldehyde which is an odor-causing substance, but also the reaction solvents used in the hydrosilylation reaction (process [V]), the water used in the odor reduction treatment process, hydrophilic solvents, and the like.

The stripping process (removal of low-boiling-point substances) may be performed on the crude product of the reaction mixture containing the (poly)oxyethylene-modified silicone as a main component as the process preceding process (W), or may be performed on the reaction mixture containing the (poly)oxyethylene-modified silicone as a main component as the process following process (W). In addition, the stripping process can be performed as the preprocessing and post processing of process [W]. The stripping process is preferably performed after the process [W], to remove propionaldehyde, which is an odor-causing substance generated by the hydrolysis reaction.

As the removal method, stripping under normal pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream. A specific example of the operation for removing low-boiling-point matter is one in which a crude product of the reaction mixture containing the (poly)oxyethylene-modified silicone containing the low-boiling-point matter as a main component is placed in a flask having a reflux cooler, a nitrogen injection port, or the like; and, while supplying nitrogen gas, the internal pressure is reduced, and the internal temperature is increased and the pressure and temperature are maintained so as to be constant. Thus, the light matter is removed. Here, typically, a pressure reduction parameter is from 0.1 to 10.0 kPa, a heating temperature is from 40 to 120° C., and a treatment time is from 10 minutes to 24 hours.

Further, after the acid treatment process, a basic substance may be used to neutralize the reaction mixture containing the (poly)oxyethylene-modified silicone as a main component. Examples of the basic substance include sodium hydroxide, potassium hydroxide, calcium hydroxide, barium hydroxide, ammonia water, sodium hydrogen carbonate, and similar inorganic salt groups; various amines, basic amino acids, and similar organic bases; and the like. The amount of the basic substance is preferably an amount needed to neutralize a reaction system comprising the reaction mixture containing the (poly)oxyethylene-modified silicone as a main component but, as necessary, the amount of the basic substance may be adjusted to an amount by which weak acidity or weak alkalinity is obtained.

In addition, an alkaline buffer may be further added in an amount corresponding to 100 ppm to 50,000 ppm to the reaction mixture containing the (poly)oxyethylene-modified silicone obtained after the acid treatment process as a main component. A minute amount of acid may be locally dissolved in the reaction mixture containing the (poly)oxyethylene-modified silicone as a main component even after a neutralization or filtration process. By adding an alkaline buffer, the liquidity of the cosmetic or the like into which the (poly)oxyethylene-modified silicone is blended is maintained on the alkali side, which makes it possible to reduce the risk of odorization caused by the impurities of the (poly)oxyethylene-modified silicone. A useful alkaline buffer is not particularly limited as long as the alkaline buffer comprises a combination of a strong base and a weak acid. Examples of the alkaline buffer include trisodium phosphate, tripotassium phosphate, trisodium citrate, sodium acetate, and other alkaline buffers. Furthermore, these alkaline buffers may be added to a cosmetic composition starting material or the like comprising a (poly)oxyethylene-modified silicone or a mixture containing the same as a main component, or they may be added to a composition at the preparation stage or after the blending of a (poly)oxyethylene-modified silicone or cosmetic composition that contains another cosmetic composition starting material or water. However, in the present invention, treatment for increasing purity using an organic wax, which is a feature of the present invention, is performed after treatment is performed in the presence of an acidic solution containing water as necessary on the (poly)oxyethylene-modified silicone or the mixture containing the same as a main component, so sufficient deodorization is achieved together with high purity. Therefore, as long as the production method of the present invention is used, the need to further add an alkaline buffer to suppress odorization over time is low.

The (poly)oxyethylene-modified silicone or the mixture containing the same as a main component can also be subjected to hydrogenation treatment as a process before or after treatment in the presence of an acidic inorganic salt in process (W). A deodorizing treatment using a hydrogenation reaction may be performed after treatment in the presence of the acidic inorganic salt of the process (W). On the other hand, the treatment in the presence of the acidic inorganic salt of the process (W) may be performed after deodorizing treatment using a hydrogenation reaction. However, hydrogenation treatment typically leads to an increase in the cost of the product over time. In the present invention, treatment for increasing purity using an organic wax, which is a feature of the present invention, is performed after treatment is performed in the presence of an acidic solution containing water as necessary on the (poly)oxyethylene-modified silicone or the mixture containing the same as a main component, so deodorization surpassing that of hydrogenation treatment is achieved together with high purity. Therefore, as long as the production method of the present invention is used, it is meaningless to further perform hydrogenation treatment for the purpose of deodorization.

A second aspect of the present invention is an external preparation, a cosmetic, or an industrial material containing the high-purity organosilicon compound obtained by the production method of the present invention.

<External Preparation/Cosmetic>

The high-purity organosilicon compound obtained by the production method of the present invention can be suitably blended into an external preparation or a cosmetic and can form the external preparation or cosmetic of the present invention. In addition, it is also possible to produce a starting material for external preparations and cosmetics containing the high-purity organosilicon compound obtained by the production method of the present invention and to blend the starting material into an external preparation or a cosmetic.

In particular, the high-purity organosilicon compound obtained by the production method of the present invention has no specific odor and demonstrates practically no odorization during formulation or over time. Moreover, there is the advantage of breaking almost no silicon-oxygen bonds which may form the main chain of the organosilicon compound and the carbon-oxygen bonds which may form the side chains. Therefore, the high-purity organosilicon compound obtained by the production method of the present invention can be suitably used as a starting material for external preparations and cosmetics used on the human body.

The high-purity organosilicon compound may also be diluted with an appropriate medium such as a silicone oil, an organic oil, or an alcohol and used as a starting material of an external preparation or a cosmetic. The proportion of the high-purity organosilicon compound in the starting material for an external preparation or a cosmetic is preferably from 10 to 100 wt. % (mass %), more preferably from 20 to 100 wt. % (mass %), and even more preferably from 30 to 100 wt. % (mass %) relative to the total weight (mass) of the starting material. The proportion of the raw material compounded in the external use preparation or the cosmetic composition is not particularly limited but, for example, can be from 0.1 to 40 wt. % (mass %), and is preferably from 1 to 30 wt. % (mass %), more preferably from 2 to 20 wt. % (mass %), and even more preferably from 3 to 10 wt. % (mass %) based on the total weight (mass) of the external use preparation or the cosmetic composition.

The high-purity organosilicon compound obtained by the production method of the present invention can be applied to applications common to the co-modified organopolysiloxanes described in Patent Document 20 (WO/2011/049248), Patent Document 21 (WO/2011/049247), and Patent Document 23 (Japanese Unexamined Patent Application Publication No. 2012-046507) or the novel organopolysiloxane copolymer described in Patent Document 22 (WO/2011/049246). In addition, the high-purity organosilicon compound obtained by the production method of the present invention can be used in the same manner as the co-modified organopolysiloxanes described in Patent Documents 20, 21, and 23 and the novel organopolysiloxane copolymer described in Patent Document 22 with regard to combinations with any cosmetic starting material components, external preparations, and, in particular, formulations, types, and formulation examples of cosmetics, and can be blended into various cosmetics or the like.

The external preparation of the present invention is not particularly limited, provided that it is a composition applied to the human body as a cosmetic or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic composition is preferably an anti-perspirant, a skin cleansing agent, a skin conditioner, a skin cosmetic composition product, a hair cleansing agent, an external use preparation for hair or a hair cosmetic composition.

The anti-perspirant, skin cleansing agent, skin external use preparation, or skin cosmetic composition of the present invention contains the high-purity organosilicon compound obtained by the production method of the present invention, and the form thereof is not particularly limited, but may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Similarly, the hair cleansing agent, hair external use preparation or the hair cosmetic composition product according to the present invention contains the high-purity organosilicon compound obtained by the production method of the present invention and can be used in various forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. There various forms can be used as shampooing agents, rinsing agents, conditioning agents, setting lotions, hair sprays, permanent wave agents, mousses, hair colorants, and the like.

In addition, the type, form, and container of the cosmetic or external preparation composition according to the present invention are the same as those disclosed in paragraphs 0230 to 0233 and the like of Patent Document 20.

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

The water that can be used in the cosmetic or external preparation of the present invention must be clean and free of components that are harmful to the human body, and examples thereof include tap water, purified water, mineral water, and deep sea water.

(Oil Agent)

The oil agent that can be used in the cosmetic or external preparation according to the present invention is preferably one or more oil agents selected from silicone oils, non-polar organic compounds, and lowly polar to highly polar organic compounds that are liquid at 5 to 100° C., and the non-polar organic compounds and lowly polar to highly polar organic compounds are preferably hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a nonsilicone-based oil agent (e.g. a hydrocarbon oil, a fatty acid ester oil, or the like), the cosmetic composition comprising a nonsilicone-based oil agent along with a silicone oil is advantageous in that a smoother, more luxurious tactile sensation is imparted.

These oil agents are the same as those disclosed in paragraphs 0130 to 0135, paragraph 0206, and the like of Patent Document 20. Examples of the fluorine-based oil include perfluoropolyether, perfluorodecalin, perfluorooctane, and the like.

(Powder or Coloring Agent)

A powder or coloring agent which can be used in the cosmetic or external preparation according to the present invention is one that is commonly used as a component of a cosmetic composition, and includes white or colored pigments and extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably one or two or more selected from an inorganic pigment powder, an organic pigment powder, and a resin powder having an average diameter in a range of 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants disclosed in paragraphs 0150 to 0152 or the like of Patent Document 20.

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. When surface treatment is performed on the high-purity organosilicon compound obtained by the production method of the present invention, uniform treatment can be performed with good treatment efficiency, so it is possible to provide a unique effect or feel corresponding to the type of the high-purity organosilicon compound without diminishing the suede-like feel of the silicone elastomer powder. Furthermore, when the high-purity organosilicon compound is blended into a cosmetic together with a silicone elastomer powder, the dispersion stability of the powder in the overall cosmetic composition is improved, and it is possible to obtain a cosmetic that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range of 0.1 to 50 μm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders, in particular, are the same as those disclosed in paragraph 0168 of Patent Document 20 and may be silicone elastomer powders that have been subjected to various surface treatments such as water-repellent treatment, as disclosed in paragraphs 0150 to 0152.

It is possible to further blend another surfactant in the cosmetic or external preparation of the present invention. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed in paragraphs 0162, 0163, 0195 to 0201, and the like of Patent Document 20. The high-purity organosilicon compound obtained by the production method of the present invention functions as a dispersant when it has polar groups and non-polar groups in the molecule. Therefore, when used in combination with a non-ionic surfactant, the high-purity organosilicon compound functions as an aid to enhance the stability of the non-ionic surfactant, and may improve the overall stability of the formulation. In particular, the high-purity organosilicon compound obtained by the production method of the present invention or a solution containing the high-purity organosilicon compound can be used in combination with a polyoxyalkylene-modified silicone, a polyglyceryl-modified silicone, a glyceryl-modified silicone, a sugar-modified silicone, and a sugar alcohol-modified silicone due to its enhanced compatibility and affinity with various modified silicones. Moreover, nonionic surfactants of these silicones in which an alkyl branch, a straight-chain silicone branch, a siloxane dendrimer branch, or the like is provided as necessary along with the hydrophilic group can also be advantageously used.

Depending on the intended use thereof, the cosmetic or external preparation of the present invention can contain one or two or more polyhydric alcohols and/or lower monohydric alcohols. These alcohols are the same as those disclosed in paragraphs 0159, 0160, and the like of Patent Document 20.

Depending on the purpose thereof, the cosmetic or the external preparation of the present invention can contain one or two or more inorganic salts and/or organic salts. These salts are the same as those disclosed in paragraph 0161 and the like of Patent Document 20.

Depending on the purpose thereof, the cosmetic or the external preparation of the present invention can contain at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax. These silicone-based components are the same as those disclosed in paragraphs 0162 to 0194 and the like of Patent Document 20.

Depending on the intended use thereof, the cosmetic or external preparation of the present invention can contain one or two or more water-soluble polymers. These water-soluble polymers are the same as those disclosed in paragraph 0201 and the like of Patent Document 20.

Depending on the intended use thereof, the cosmetic or external preparation of the present invention can contain one or two or more ultraviolet light blocking components. These ultraviolet light blocking components are the same as the organic and inorganic ultraviolet light blocking components disclosed in paragraphs 0202 to 0204 and the like of Patent Document 20, but specifically, an ultraviolet light blocking component that can be suitably used is at least one selected from a group consisting of microparticulate titanium oxide, microparticulate zinc oxide, 2-ethylhexyl p-methoxycinnamate, 4-tert-butyl-4'-methoxydibenzoylmethane, diethylamino hydroxybenzoyl hexyl benzoate, benzotriazole-based UV absorbers, and triazine-based UV absorbers such as 2,4,6-tris[4-(2-ethylhexyloxycarbonyDanilino]1,3,5-triazine (INCI: octyl triazone) and 2,4-bis([4-(2-ethyl-hexyloxy)-2-hydroxy]phenyl)-6-(4-methoxyphenyl)-1,3,5-triazine (INCI: bis-ethylhexyloxyphenol methoxyphenyl triazine, trade designation: Tinosorb®S). These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with the high-purity organosilicon compound in the cosmetic or the external preparation of the present invention, it is possible to stably disperse the ultraviolet light blocking component in the cosmetic composition while improving the feeling to touch and storage stability of the overall cosmetic composition, and it is therefore possible to impart the cosmetic composition with excellent ultraviolet light blocking properties.

Various components other than the components described above can be used in the cosmetic composition or external use preparation of the present invention, provided that such use does not impair the effects of the present invention. Examples thereof include oil-soluble gelling agents, organomodified clay minerals, preservatives, bioactive components, skin beautifying components, pH adjusting agents, antioxidants, solvents, chelating agents, moisturizing components, perfumes and the like. These optional components for a cosmetic product are the same as those disclosed in paragraphs 0207, 0208, 0220 to 0228, and the like of Patent Document 20.

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent. These anti-perspiration components and deodorant components are the same as those disclosed in paragraphs 0209 to 0219 and the like of Patent Document 20. Similarly, in cases in which the cosmetic or external preparation according to the present invention is an anti-perspirant composition, the preparation, method of use, and the like of the various anti-perspirant compositions are the same as those disclosed in paragraphs 0234 to 0275 and the like of Patent Document 20.

Industrial Applicability

The production method for a high-purity organosilicon compound according to the present invention can be applied regardless of the type of the organic modifier, is inexpensive and simple, has excellent yield or productivity, and can reasonably accommodate production on a commercial scale. In addition, the high-purity organosilicon compound obtained by the production method of the present invention essentially consists of a single component from which impurities—in particular, impurities originating from the organic modifier—have been removed, so phase separation, precipitation of the unreacted starting material, or the like does not occur after production. In particular, the high-purity organosilicon compound obtained by the production method of the present invention maintains an appearance with high transparency, regardless of the temperature environment in which it is used, so even when the compound is used or various industrial materials such as oil agents into which the compound is blended are used in cold regions, problems such as decreases in performance or fluctuations in quality due to poor compatibility between the main component and the impurities do not occur, and the production process can thus be stabilized. Conversely, even when the compound is used or various industrial materials such as oil agents into which the compound is blended are used in hot seasons or regions, problems such as decreases in performance or fluctuations in quality due to poor compatibility between the main component and the impurities do not occur, and the compound is unlikely to be affected by degradation due to oxidation or the like, so it is possible to stabilize the production process as well as to improve the quality level of the final product. Therefore, the present invention solves the basic problems of organomodified silicones and organomodified silanes which are difficult to prepare with high purity using conventional methods.

Specifically, the high-purity organosilicon compound obtained by the present invention can not only be suitably used as a starting material for an external preparation, a medicament, or a cosmetic, but it can also be suitably used as a fiber treatment agent, a varnish or paint additive having excellent heat resistance, weather resistance, and electrical properties, a coating agent, a primer, a tackifier, a polyol main agent, foam stabilizer, or modifier for various urethanes or foaming materials, a mold release agent or peeling agent, an antifoam agent, a grease or oil compound, an oil for insulation, burnishing, water repellency, a heating medium/cooling medium, or lubrication, a modifier, additive, or surface treatment agent for a rubber or resin, a starting material for a silicone-modified organic resin, a compounding agent, modifer, or precursor for a silane coupling agent, a coating material or sealing material for architectural use or a lining, a protecting agent, lubricant, or buffer for optical fibers or electrical lines, and a starting agent for general industrial materials such as electronic/electrical parts.

EXAMPLES

The present invention will be described in detail hereinafter using working examples and comparative examples, but the present invention is not limited to the working examples described below.

Note that in the production examples and comparative examples below, the language "production of polyether-modified silicone No. X" is used for the sake of convenience, but the obtained products are in the form of mixtures containing a small amount of unreacted starting material and the like in addition to the main components.

In the following compositional formulae, "Me" represents a methyl (—$CH_3$) group, "M" represents a $Me_3SiO$ group (or an $Me_3Si$ group), "D" represents an $Me_2SiO$ group, "$D^H$" represents an MeHSiO group, and "$M^R$" and "$D^R$" respectively represent units in which a methyl group in "M" or "D" is modified by any substituent. Additionally, in the production examples, "IPA" represents isopropyl alcohol.

Production Example 1

<Production of Polyether—Modified Silicone No. 1>
Step 1: First, 15.801 kg of a methylhydrogenpolysiloxane expressed by the average composition formula $MD_{37}D^H{}_{13}M$, 16.9 g of a vinyl tris (trimethylsiloxy)silane expressed by the average composition formula $CH_2$=CH—$Si(OSiMe_3)_3$, and 33.1 g of an IPA solution of a platinum-1,3-divinyl-1,1,3,3-tetramethyldisiloxne complex (Pt concentration: 0.45 wt. %) were charged into a reaction vessel, and heating was started while stirring under a nitrogen stream. After a reaction was performed for 2.5 hours at 50 to 75° C., the reaction liquid was collected, and an alkali decomposition gas generation method (the remaining Si—H groups are decomposed using a KOH ethanol/water solution, and the reaction rate is calculated from the volume of the produced hydrogen gas) was used to confirm that the reaction was proceeding as planned.

Step 2: The reaction liquid was set to 48° C., and when 1.42 g (first time) of dodecene (α-olefin purity=95.4%) was added, an increase in temperature to 65° C. was observed. When 1.46 kg (second time) of dodecene (α-olefin purity=95.4%) was added at the point when the temperature of the reaction liquid dropped to 52° C., an increase in temperature to 67° C. was observed. When 1.84 kg (third time) of dodecene (α-olefin purity=95.4%) was added at the point when the temperature of the reaction liquid dropped to 53° C., an increase in temperature to 71° C. was observed. When 1.83 kg (fourth time) of dodecene (α-olefin purity=95.4%) was added at the point when the temperature of the reaction liquid dropped to 55° C., an increase in temperature to 75° C. was observed. The total reaction time in step 2 was 2.5 hours. The reaction liquid was collected and the reaction was confirmed to be proceeding as planned with the same method as in step 1.

Step 3: First, 4.77 kg of a polyoxyethylene (9.5) monoallyl ether, 3.0 g of natural vitamin E, and 2.8 kg of IPA were added to the reaction liquid, and 33.3 g of the same platinum catalyst solution as described above was additionally added. A reaction was performed for 1.5 hours at 60 to 70° C., and when confirmed with the same method as in step 1, the reaction rate indicated that the reaction was roughly completed. Here, the charged amount of the polyoxyethylene (9.5) monoallyl ether was over 1.16 times the molar amount of the Si—H groups (for $D^H{}_2$ units) of the methylhydrogen-polysiloxane. Therefore, the excess unreacted polyether remains in the reaction liquid.

Step 4: First, 1.45 kg (fifth time) of dodecene (α-olefin purity=95.4%) was added, and when a reaction was performed for three hours at 50 to 70° C. and then confirmed with the same method as in step 1, the reaction was compete.

Step 5: The reaction liquid was heated under reduced pressure and held for five hours under conditions at 135 to 145° C. and 25 to 55 mmHg while bubbling due to nitrogen gas, and the low-boiling-point matter such as dodecene was distilled out. When the pressure was then restored after cooling to 75° C. or lower, the content of the reaction vessel was a light brown, uniform liquid with a slight feeling of transparency.

Step 6: An aqueous solution prepared by dissolving 4.5 g of a sodium hydrogen sulfate monohydrate in 450 g of ion-exchanged water was charged into the content of the reaction vessel, and acid treatment was performed for one hour at 60 to 70° C. while stifling under a nitrogen stream. The pressure was then reduced at 60° C., and the pressure was restored when the distillation of water and other low-boiling-point matter stopped (first cycle of acid treatment). Next, 450 g of water was added, and after treatment was performed for ten minutes, the pressure was similarly reduced and then restored when the distillation of water and other low-boiling-point matter stopped (second cycle of acid treatment). After 450 g of water was once again added and acid treatment was performed for 1.3 hours, the pressure was similarly reduced. A heated, depressurized state was maintained for 12 hours at 60 to 75° C., and the pressure was restored after the water droplets in the system disappeared (third cycle of acid treatment). As a result, 28.2 kg of a composition containing a polyether-modified silicone represented by the average composition formula $MD_{37}D^{R*11}{}_{10}D^{R*31}{}_1 D^{R*21}{}_2 M$ was obtained as a grayish brown, opaque, cloudy liquid. (Yield=100×28.2/30.0=94.0%)

Here, $R^{*11}$, $R^{*21}$, and $R^{*31}$ are as follows.
$R^{*11}$=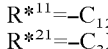—$C_{12}H_{25}$
$R^{*21}$=—$C_3H_6O(CH_2CH_2O)_{9.5}$—H
$R^{*31}$=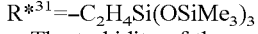—$C_2H_4Si(OSiMe_3)_3$ The turbidity of the appearance of the content increased dramatically due to acid treatment, but this is considered to be due to the result of a greater increase in polarity and a decrease in the compatibility with the modified silicone serving as the main component as the unreacted unsaturated polyether (monool) was hydrolyzed and transformed into a corresponding polyethylene glycol (diol).

Comparative Example 1

<Preparation of Comparative Composition RE-1 Containing Polyether-Modified Silicone No. 1>
First, 20 kg of the grayish brown, opaque, uniform liquid obtained in Production Example 1 was filtered with a pressure filter at room temperature and an N2 pressure of 150 kPa using 100 g of Hiflo Super Cell (Celite Corporation, flux calcined diatomaceous earth) and 50 g of Filter Cell (Celite Corporation, natural diatomaceious earth) as filter aids and using ADVANTEC No. 424 (diameter: 28 mm, Toyo Roshi Co., Ltd.) as filter paper. Immediately after filtration was begun, a filtrate with transparency emerged, but once approximately 2 kg of the filtrate emerged, a cloudy liquid leaked out within one hour. As a result, 19.5 kg of a grayish brown, opaque, cloudy liquid was obtained over the course of ten hours. (Yield=19.5/20=97.5%) This composition exhibited no improvement in the transparency of the appearance whatsoever in comparison to the composition obtained in Production Example 1. That is, with the technique of Comparative Example 1, rarefaction equivalent to only approximately 10% of the total amount of the reaction mixture obtained in Production Example 1 could be obtained. Here, the total amount of treatment liquid/filtration area=20,000 g/615 cm²=32.5; total filtration time=10 hr; and transparent filtrate/filtration area=2,000 g/615 cm²=3.25.

Comparative Example 2

<Preparation of Comparative Composition RE-2 Containing Polyether-Modified Silicone No. 1>

Next, 2.1 g of the grayish brown, opaque, uniform liquid obtained in Comparative Example 1 was extracted and pressure-filtered at an N2 pressure of 150 kPa using a specialized filter with a Zeta Plus Filter 30C (diameter: 90 mm, 3M Corporation, zeta-potential adsorption filter). At this time, filtration was very slow at room temperature, so filtration was performed while maintaining a temperature of from 40 to 50° C. Approximately 700 g of the initial filtrate improved to a roughly transparent appearance, but it took five hours to achieve this improvement. Turbidity appeared thereafter, so the composition was mixed so that the entire amount of the filtrate that was ultimately obtained was uniform, and as a result, 2.0 kg of a grayish, light brown, opaque, uniform liquid was obtained. (Yield=2.0/2.1=95.2%) This composition exhibited a slight improvement in the transparency of the appearance in comparison to the composition obtained in Production Example 1 (Comparative Example 1). That is, with the technique of Comparative Example 2, rarefaction equivalent to only approximately 33% of the total amount of the reaction mixture obtained in Production Example 1 could be obtained. Here, the total amount of treatment liquid/filtration area=2,100 g/63.6 cm²=33.0; total filtration time=15 hr; and transparent filtrate/filtration area=700 g/63.6 cm²=11.0.

Working Example 1

<Preparation of High-Purity Polyether-Modified Silicone No. 1>

First, 2.9 g of the grayish brown, opaque, uniform liquid obtained in Comparative Example 1 and 22.7 g of a flaked product (organic wax) of PEG#20000 (polyethylene oxide with a molecular weight of 20,000, melting point: approximately 65° C.) were charged into a flask, and heating was started while stirring under a nitrogen stream. When mixing and stifling were performed aggressively for 40 minutes at 90° C., the appearance was a cloudy white, uniform dispersion. The composition was then left to cool (2.5 hours) while stirring until the temperature reached 40° C. or lower, and treatment was ended. The appearance of the flask content was the same as described above. Next, the flask content was filtered with a pressure filter at room temperature and an N₂ pressure of 150 kPa using 10 g of Hiflo Super Cell (Celite Corporation, flux calcined diatomaceous earth) as a filter aid and using ADVANTEC No. 424 (diameter: 110 mm, Toyo Roshi Co., Ltd.) as filter paper. As a result, a completely transparent, uniform, light yellow filtrate was surprisingly obtained from start to finish, and the total amount was 2.83 kg. (Yield=2.83/2.9=97.6%) That is, with the technique of the present invention demonstrated in Working Example 1, it was possible to achieve the rarefaction of the entire amount of the reaction mixture obtained in Comparative Example 1. Here, the total amount of treatment liquid/filtration area=2,900 g/95.0 cm²=30.5; total filtration time=14 hr; and transparent filtrate/filtration area=2,830 g/95.0 cm²=30.8.

Working Example 2

<Preparation of High-Purity Polyether-Modified Silicone No. 1 (2)>

First, 829 g of the grayish brown, opaque, cloudy liquid obtained in Comparative Example 1, 24.9 g of a flaked product (organic wax) of PEG #20000 (polyethylene oxide with a molecular weight of 20,000, melting point: approximately 65° C.), and 80 g of isooctane serving as a diluent were charged into a 1 L flask, and heating was started while stirring under a nitrogen stream. When mixing and stirring were performed aggressively for 50 minutes at 70 to 95° C., the appearance was a cloudy white, uniform dispersion. The composition was then left to cool (two hours) while stifling until the temperature reached 40° C. or lower, and treatment was ended. The appearance of the flask content was similar to that described above, but there was an increase in whiteness, and a white sediment was also observed at the base of the flask. Next, the flask content was filtered with a pressure filter at room temperature and an N2 pressure of 150 kPa using 10 g of Hiflo Super Cell (Celite Corporation, flux calcined diatomaceous earth) as a filter aid and using ADVANTEC No. 424 (diameter: 110 mm, Toyo Roshi Co., Ltd.) as filter paper. As a result, a completely transparent, uniform filtrate was surprisingly obtained from start to finish, and the total amount was 796 g. (Filtration time=2.5 hr) Next, 744 g of this composition was collected and charged into a clean 1 L flask. This was heated under reduced pressure and held for 1 hour and 15 minutes under conditions at 105 to 115° C. and 10 mmHg or lower while bubbling due to nitrogen gas so as to distill out the low-boiling-point matter. When the pressure was then restored, it was observed that 683 g of a completely transparent, light yellow liquid was obtained. That is, with the technique of the present invention demonstrated in Working Example 2 as well, it was possible to achieve the rarefaction of the entire amount of the reaction mixture obtained in Comparative Example 1.

Comparative Example 3

<Preparation of Comparative Composition RE-3 Containing Polyether-Modified Silicone No. 2>

Step 1: First, 751.1 g of a methylhydrogenpolysiloxane expressed by the average composition formula $MD_{45}D^H{}_2M$, 249 g of a polyoxyethylene (9.5) monoallyl ether, 300 g of toluene, and 2.0 g of a 5 wt. % methanol solution of sodium acetate were charged into a reaction vessel, and heating was started while stifling under a nitrogen stream. When the liquid temperature reached 70° C., 0.20 ml of an IPA solution of chloroplatinic acid (platinum concentration: 3.7 wt. %) was added. An increase in temperature to 85° C. occurred due to heat generation, and the appearance of the reaction liquid had changed to a roughly transparent appearance after 30 minutes. When the reaction liquid was collected and confirmed by an alkali decomposition gas generation method, the reaction was complete. Here, the charged amount of the polyoxyethylene (9.5) monoallyl ether was over 1.26 times the molar amount of the Si—H groups (for $D^H{}_2$ units) to be reacted. Therefore, the excess unreacted polyether remains in the reaction liquid.

Step 2: First, 3.0 g of baking soda was added, and after the composition was neutralized by mixing and stifling for one hour at 75 to 80° C., the reaction mixture was heated under reduced pressure and held for 1.5 hours under conditions at 120 to 125° and 10 mmHg or lower while bubbling due to nitrogen gas so as to distill out low-boiling-point matter such as toluene. The pressure was then restored after cooling to 70° C. or lower, and 920 g of a light yellow, transparent, uniform liquid was obtained as a result of performing filtration with a pressure filter at room temperature and an N2 pressure of 150 kP using 10 g of Hiflo Super Cell (Celite Corporation, flux calcined diatomaceous earth) as a filter aid and using ADVANTEC No. 424 (diameter: 110 mm, Toyo Roshi Co., Ltd.) as filter paper.

Step 3: Next, 600 g of this filtrate was transferred to a 1 L autoclave, and after 30 g of a sponge nickel catalyst, 15 g of water, and 15 g of IPA were added, hydrogen gas was introduced. After a hydrogenation reaction was performed for six hours at a temperature of 140° C. and a pressure of 80 kg/cm$^2$, the resulting reactive product was cooled to 60° C. and restored to normal pressure. Next, 6 g of activated carbon was mixed into the composition, and the sponge nickel catalyst was removed by precision filtration to obtain 530 g of a colorless, transparent filtrate.

Step 4: This filtrate was charged into a 1 L flask, heated under reduced pressure, and held for three hours under conditions at 70 to 75° C. and 10 mmHg or lower while bubbling due to nitrogen gas so as to distill out low-boiling-point matter, and 500 g of a composition containing a polyether-modified silicone represented by the average composition formula $MD_{45}D^{R*21}{}_2M$ was obtained as a colorless, transparent, uniform liquid.

Here, $R^{*21}$ is as follows.
$R^{*21}=-C_3H_6O(CH_2CH_2O)_{9.5}-H$

In addition, due to the fact that acid treatment was not performed in Comparative Example 3 and the fact that the wt. % of the polyether part of the polyether-modified silicone, which is a copolymer, was greater than in Production Example 1, and the polarity of the modified silicone was therefore greater than in Production Example 1, it is thought that the compatibility of the unreacted polyether (monool) and the modified silicone was good and that a composition with a transparent appearance was therefore obtained in Comparative Example 3.

The contents of "high-purity polyether-modified silicone No. 1 and high-purity polyether-modified silicone No. 1 (2)", which are high-purity organosilicon compounds of the present invention, and "comparative compositions RE-1 and RE-2 containing polyether-modified silicone No. 1 and comparative composition RE-3 containing polyether-modified silicone No. 2" of the comparative examples are shown in the following Table 1.

TABLE 1

| Sample | Appearance | Transparent filtrate/filtration area [g/cm$^2$] | Chemical structure main component*[2] |
|---|---|---|---|
| Working Example 1 | Light yellow, transparent, uniform liquid | >30.8 | $MD_{37}D^{R*11}{}_{10}D^{R*31}{}_1D^{R*21}{}_2M$ |
| Working Example 2 | Light yellow, transparent, uniform liquid | —*[1] | |
| Comparative Example 1 | Grayish brown, opaque, cloudy liquid | 3.25 | |
| Comparative Example 2 | Grayish, light brown, opaque, uniform liquid | 11.0 | |
| Comparative Example 3 | Colorless, transparent, uniform liquid | —*[1] | $MD_{45}D^{R*21}{}_2M$ |

Note
*[1] The numerical value of the [total amount of the treatment solution/filtration area] different from other experiments and was therefore omitted.
Note
*[2] The chemical structure of the polyether-modified silicone serving as the main component is expressed by the average composition formula.

In the table, the structures and types of the functional groups are as follows.
≤Group having a Siloxane Dendron Structure: $R^{*3}$>
$R^{*31}=-C_2H_4Si(OSiMe_3)_3$
<Oxyethylene Group: $R^{*2}$>
$R^{*21}=-C_3H_6O(CH_2CH_2O)_{9.5}-H$
<Other Organic Groups: $R^{*1}$>
$R^{*11}=-C_{12}H_{25}$

[Measurement of total carbonyl amount] The total carbonyl amounts of the polyether-modified silicones (samples) obtained in Working Examples 1 and 2 and Comparative Examples 2 and 3 were measured as "carbonyl values (COV)" in accordance with the following procedure so as to qualitatively evaluate carbonyls, which cause the odor of the composition.

Preparation Example 1A

Reagent special-grade n-butanol (A) was measured in a 100 mL brown glass vial, and 4.3 g of reagent special-grade trichloroacetic acid was further added. After a lid was placed on the vial, the mixture was shaken and homogenized so as to prepare an alcohol solution of trichloroacetic acid (acid concentration: 4.3% (wt/vol). This solution is defined as "trichloroacetic acid solution (1A)" hereafter. This preparation operation was performed within three hours prior to the measurement of light absorbance.

Preparation Example 2A

Reagent special-grade n-butanol (A) was measured in a 100 mL brown glass vial, and 50 mg of 2,4-dinitrophenylhydrazine (reagent special-grade product containing an equal amount of water; abbreviated as "2,4-DNPH" hereafter) was further added. After a lid was placed on the vial, the vial was placed in an ultrasonic washer for ten minutes so as to completely dissolve the 2,4-DNPH with the alcohol (A), and a 0.025% (wt/vol) alcohol solution of 2,4-DNPH was thus prepared. This solution is defined as "2,4-DNPH solution (2A)" hereafter. This preparation operation was performed within three hours prior to the measurement of light absorbance.

Preparation Example 3B

Reagent special-grade ethanol (B) was measured in a 100 mL brown glass vial, and 4.0 g of potassium hydroxide (pellet-shaped reagent special-grade product) was further added directly. After a lid was placed on the vial, the vial was placed in an ultrasonic washer for 20 minutes so as to completely dissolve the potassium hydroxide with the alcohol (B), and a 4.0% (wt/vol) alcohol solution of potassium hydroxide was thus prepared. This solution is defined as "potassium hydroxide solution (3B)" hereafter. This preparation operation was performed within three hours prior to the measurement of light absorbance.

(Measurement of Carbonyl Value)

First, 2.00 g of a sample and 23.00 g of the reagent special-grade butanol (A) were charged into a 50 mL screw tube with a lid, and these were mixed so as to prepare 25.00 g of a sample solution (Sa) with a sample concentration of 8 mass %.

Next, 1.250 g of the obtained sample solution (Sa) and 3.750 g of the reagent special-grade n-butanol (A) were charged into a 50 mL volumetric flask, and both were mixed so as to prepare 5.000 g of a sample solution (Sb) with a sample concentration of 2 mass %.

Next, 3 mL of the trichloroacetic acid solution obtained in Preparation Example 1A and 5 mL of the 2,4-DNPH solution (2A) obtained in Preparation Example 2A were added with a transfer pipet to the volumetric flask containing 5.000 g of the sample solution (Sb). Further, 1.050 g of purified water was added and mixed. This is to hydrolyze precursors of carbonyl compounds such as acetal which may be present in the sample and to detect the precursors as carbonyls.

Next, a stopper was placed in the volumetric flask, and after air tightness was secured by wrapping a Teflon (registered trademark) seal around the stopper, the volumetric flask was placed in a constant-temperature bath at 60° C. and heated for 30 minutes so as to react the carbonyls contained in the sample and the 2,4-DNPH. Next, the volumetric flask was removed from the constant-temperature bath and left to stand for 30 minutes at room temperature.

Next, the stopper of the volumetric flask was removed, and 10 mL of the potassium hydroxide solution (3B) obtained in Preparation Example 3B was added with a transfer pipet and mixed by shaking the volumetric flask. Eight minutes after 10 mL of the potassium hydroxide solution (3B) was added, the reagent special-grade n-butanol (A) was added as a dilution solvent, and this system was shaken to prepare a reaction solution with a total volume of 50 mL (basic reaction solution). Next, 15 minutes after 10 mL of the potassium hydroxide solution (3B) was added, the reaction solution was placed in an absorption cell (liquid layer length=1 cm), and the absorbance ($A_1$) at 430 nm was measured with an absorptiometer.

On the other hand, as a blank test, a solution obtained by performing the same operation as described above (addition of the trichloroacetic acid solution (1A), addition of the 2,4-DNPH solution (2A), heating and cooling of the obtained mixed solution, addition of the potassium hydroxide solution (3B), and addition of a dilution solvent containing the reagent special-grade n-butanol (A)) using 5.000 g of the reagent special-grade n-butanol (A) instead of the sample solution (Sb) was placed in an absorption cell (liquid layer length=1 cm), and the absorbance ($A_2$) at 430 nm was measured in the same manner as described above.

The absorbance ($A_1$) and the absorbance ($A_2$) obtained as described above were substituted into the numerical formula: $CV=(A_1-A_2)/0.1$ so as to find the carbonyl value (COV).

The evaluation results of the total carbonyl amounts (COV) of the polyether-modified silicones obtained in Working Examples 1 and 2 and Comparative Examples 2 and 3 are shown in the following Table 2. The high-purity polyether-modified silicones of Working Examples 1 and 2 of the present invention achieved a level in which the COV was almost completely zero, which clearly surpassed the technical level of hydrogenation methods typically considered to be satisfactory. The COV is approximately 0.3 in Comparative Examples 2 and 3, but this is equivalent to approximately 80 ppm in terms of the amount of propanol. Therefore, when the polyether-modified silicone compositions of Comparative Examples 2 and 3 are blended into cosmetics or external preparations containing water, low-molecular-weight odor substances originating from an equivalent of 80 ppm of propanol may be ultimately generated over time. The level of 80 ppm is a sufficiently high concentration for detection by means of the human sense of smell. On the other hand, in Working Examples 1 and 2, the total amounts of odor-causing substances were suppressed by two orders of magnitude from this level, and a level of essentially zero (≤0.8 ppm) was reached. In this way, there is not only a difference in the purity of the main components between the Working Examples and the Comparative Examples, but there is also a 100-fold difference in the attained odor level, and these differences validate the excellence of the present invention.

TABLE 2

| Sample | Polyether-modified silicone structure | Odor reduction Treatment | Purification-increasing treatment | COV (Abs/g) |
|---|---|---|---|---|
| Working Example 1 | $MD_{37}D^{R*11}{}_{10}D^{R*31}{}_1D^{R*21}{}_2M$ | $NaHSO_4$ water treatment | ○ (yes) | 0.02 |
| Working Example 2 | | $NaHSO_4$ water treatment | ○ (yes) | N.D. |
| Comparative Example 2 | Same as above | $NaHSO_4$ water treatment | X (no) | 0.29 |
| Comparative Example 3 | $MD_{45}D^{R*21}{}_2M$ | Hydrogenation | X (no) | 0.34 |

In the table, the structures and types of the functional groups are as follows.

<Group having a Siloxane Dendron Structure: $R^{*31}$>
$R^{*31}=-C_2H_4Si(OSiMe_3)_3$
<Oxyethylene Group: $R^{*2}$>
$R^{*21}=-C_3H_6O(CH_2CH_2O)_{9.5}-H$
<Other Organic Groups: $R^{*1}$>
$R^{*11}=-C_{12}H_{25}$

[Odor accelerated test] Polyether-modified silicones are known to tend to develop a unique odor over time in a formulation containing water and a specific polyhydric alcohol. Therefore, samples having the compositions shown in Table 3 were produced and stored under accelerated conditions of one week at 70° C. The samples were then returned to room temperature and unsealed, and functional evaluations were performed on the potency and amount of the odor produced using the sense of smell.

TABLE 3

| No. | Starting material name | Mass [g] |
|---|---|---|
| 1 | Polyether-modified silicones of Working Examples 1 and 2 or Comparative Examples 2 and 3 | 3.0 |
| 2 | 1,3-Butylene glycol | 3.0 |
| 3 | Purified water | 24.0 |
| Total | | 30.0 |

[Preparation of Samples for Accelerated Tests]
1. The starting materials (Nos. 1 to 3) shown in Table 3 were charged into a 50 ml screw tube, and the tube was stopped and shaken well. Samples were produced for each of the polyether-modified silicones obtained in the working examples and the comparative examples. (Total of 4 samples)
2. Only the starting materials of Nos. 2 and 3 were charged into a separate 50 ml screw tube, and the tube was stopped and shaken well so as to prepare a blank sample. (Total of 1 sample)
3. The samples described above were left to stand for one week in a constant-temperature bath at 70° C.

[Odor Test]
The samples left to stand for one week in a constant-temperature bath at 70° C. as described above were removed after 1 day and after 7 days and returned to room temperature, and the degree of the specific odor when unsealed was evaluated by the sense of smell in accordance with the following criteria.
Odor test evaluation criteria:
⊚: No specific odor is perceived whatsoever.
○: A specific odor is perceived very slightly.
Δ: A specific odor is observed slightly.
X: An unpleasant solvent odor is clearly observed.
XX: A strong and very unpleasant solvent odor is observed.

[Odor test results] The results of odor acceleration tests in the formulations are shown in the following Table 4 together with the COV of the polyether-modified silicones. The high-purity polyether-modified silicones of the present invention used in Working Examples 1 and 2 demonstrated odorlessness of the same level as the hydrogenated product (Comparative Example 3) and the blank without silicone under the accelerated test conditions of the formulation. On the other hand, although the sample using Comparative Example 2 prepared by performing only acid treatment with $NaHSO_4$/water had a COV value approximately the same as the sample using Comparative Example 3 as a hydrogenated product, it was confirmed that a strong odor was generated at the initial stage of the acceleration tests. These phenomena are understood as follows. When only acid treatment is performed, the excess unsaturated polyether contained in the polyether-modified silicone composition or acetal compound originating from the unsaturated polyether is not completely decomposed. The proof of this is the numerical value of COV=0.29 (approximately 80 ppm in terms of propanol). In addition, it is thought that a minute amount of acid is transferred to and dissolved in the sample of Comparative Example 2. As a result, the formulation becomes acidic, so conditions advantageous for hydrolyzation were also achieved from the perspective that the composition was diluted and left at a high temperature. Therefore, hydrolyzation was completed in only one day, and low-molecular-weight odor components originating from propanol were generated at once. Once the screw tube was unsealed to confirm the odor, most of the odor components volatilized in the atmosphere and disappeared. Even if aging is continued further, there are no precursors with an odor that should be hydrolyzed, which may be why only the residual odor from day 1 was detected in the confirmation after 7 days. On the other hand, the sample of Comparative Example 3, which is a hydrogenated product, is treated with alkali water due to the activation of the surface of the sponge nickel catalyst for hydrogenation, so it contains a minute alkali content even if the metal catalyst itself is completely removed. Therefore, the formulation also becomes alkaline, resulting in conditions in which the hydrolysis of acetal compounds does not occur. In general, unsaturated groups completely disappear due to hydrogenation, but acetal compounds are not decomposed for the most part and remain in the polyether-modified silicone composition. The proof of this is the numerical value of COV=0.34 (approximately 80 ppm in terms of propanol). In particular, when the formulation is acidic, low-molecular-weight odor substances originating from propanol may be ultimately generated in an amount equivalent to 80 ppm over time. In contrast, it can be seen that the high-purity polyether-modified silicones of the present invention used in Working Examples 1 and 2 demonstrate excellent properties from the perspective of the COV value and the perspective of the odor acceleration tests.

TABLE 4

| Sample | Polyether-modified silicone structure | Odor test After 1 day | Odor test After 7 days | COV (Abs/g) |
|---|---|---|---|---|
| Working Example 1 (High-purity product) | $MD_{37}D^{R*11}_{10}D^{R*31}_{1}D^{R*21}_{2}M$ | ⊚ - ○ | ⊚ - ○ | 0.02 |
| Working Example 2 (High-purity product) | | ⊚ | ⊚ | N.D. |
| Comparative Example 2 | Same as above | X | ○ - Δ | 0.29 |
| Comparative Example 3 | $MD_{45}D^{R*21}_{2}M$ | ⊚ - ○ | ⊚ - ○ | 0.34 |
| Blank | — (no silicone) | ⊚ | ⊚ | — (0) |

In the table, the structures and types of the functional groups are as follows.

<Group having a Siloxane Dendron Structure: $R^{*31}$>
$R^{*31}$=–$C_2H_4Si(OSiMe_3)_3$
<Oxyethylene Group: $R^{*2}$>
$R^{*21}$=–$C_3H_6O(CH_2CH_2O)_{9.5}$—H
<Other Organic Groups: $R^{*1}$>
$R^{*11}$=–$C_{12}H_{25}$ It can be seen from the above results that the samples of the working examples are far superior to the samples of the comparative examples from the perspectives of high purity and odorlessness.

Hereinafter, formulation examples of the cosmetic composition and the external use preparation according to the present invention are described, but the cosmetic composition and the external use preparation according to the present invention are not limited to the types and compositions recited in these formulation examples.

The high-purity organosilicon compound obtained by the present invention can be used in various external preparations and cosmetics, for example. A specific formulation example thereof is one in which components corresponding to silicone compound Nos. 1 to 16 in Formulation Examples 1 to 43 of various cosmetics and external preparations described in Patent Document 20 (WO/2011/049248) and/or various polyether-modified silicones are substituted with the high-purity organosilicon compounds of the present invention (high-purity organosilicon compound No. 1 and the like) or solutions thereof.

In addition, a specific formulation example thereof is one in which components corresponding to silicone compound Nos. 1 to 14 in Formulation Examples 1 to 24 of various cosmetics and external preparations disclosed in Patent Document 21 (WO/2011/049247) and/or various polyether-modified silicones are substituted with the high-purity organosilicon compounds of the present invention (high-purity organosilicon compound No. 1 and the like) or solutions thereof.

Yet another formulation example is one in which components corresponding to the AB-type organopolysiloxane copolymers P1 to P6 contained in Formulation Examples 1 to 10 of various cosmetics and external preparations disclosed in Patent Document 22 (WO/2011/049246) (Synthesis Examples 1 to 12) and/or various oxyethylene-modified silicones are substituted with the high-purity organosilicon compounds of the present invention (high-purity organosilicon compound No. 1 and the like) or solutions thereof.

In addition, another formulation example is one in which components corresponding to silicone compound Nos. 1 to 8 contained in Formulation Examples 1 to 14 of various cosmetics and external preparations disclosed in Patent Document 23 (Japanese Unexamined Patent Application Publication No. 2012-046507) and/or various polyether-modified silicones are substituted with the high-purity organosilicon compounds of the present invention (high-purity organosilicon compound No. 1 and the like) or solutions thereof.

The high-purity organosilicon compound of the present invention has the advantage that, since an organic modifier with a polarity substantially differing from that of the organosilicon compound is removed, problems related to poor compatibility at the time of the addition of various starting materials are unlikely to occur when designing a formulation for a cosmetic or external preparation, so the scope of formulation design widens. At the same time, it is also possible to reduce the risk or concerns related to the stability of the final product. Since the composition has high purity, it is advantageous from the perspectives of the tactile feel improving effect, moisturizing effect, minimal degradation phenomena such as odorization over time, surface active effect, emulsification performance, powder dispersion stability, powder surface treatment effect, or the duration of these effects in comparison to typical organosilicon compounds with large impurity content. In particular, in a formulation containing a powder or a formulation containing a small amount of water, the characteristics of the high-purity organosilicon compound obtained by the present invention make it possible to finely disperse medicinal components or powders into a cosmetic or external preparation more stably than with conventional methods. As a result, a substantial advantage arises in that the effects of the original formulation are amplified, such as an improvement in evenness in application, in cosmetic duration or coloring or an improvement in a skin care or UV filter effect. In addition, in a formulation not containing a powder, the characteristics of the high-purity organosilicon compound obtained by the production method of the present invention make it possible to easily obtain a stable product with excellent transparency, even if the composition has low viscosity.

The invention claimed is:

1. A production method for a liquid high-purity organosilicon compound, the method comprising the steps of:
   adding, to a mixture containing an organosilicon compound modified by an organic modifier having a (poly)oxyethylene site selected from the group consisting of organomodified silicones having an organic modified group containing a (poly)oxyethylene site and organomodified silanes having an organic modified group containing a (poly)oxyethylene site and impurities originating from the organic modified group, an organic wax having a (poly)oxyethylene site having affinity with the impurities and having a higher melting point than the organosilicon compound, melting and mixing while heating, and introducing the impurities into the melted organic wax;
   obtaining a solidified product of the organic wax by cooling the organic wax; and
   performing solid/liquid phase separation on the organosilicon compound and the solidified product of the organic wax.

2. The production method according to claim 1, wherein the organosilicon compound is a liquid at least at 100° C.

3. The production method according to claim 1, wherein the organic wax has a melting point of from 45° C. to 150° C.

4. The production method according to claim 1, wherein the organic wax has an average molecular weight of at least 900.

5. The production method according to claim 1, wherein silicon atoms of the organosilicon compound bond with organic modified groups via Si—C bonds or Si—O—C bonds.

6. The production method according to claim 1, wherein the organosilicon compound is a compound of Formula (1):

(1)

wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having 9 to 60 carbon atoms, or the chain organosiloxane group of Formula (2-1):

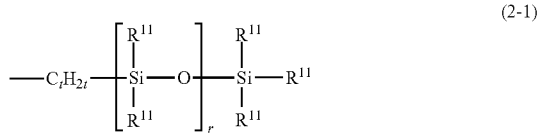

$$\text{—C}_t\text{H}_{2t}\text{—}\left[\begin{array}{c}R^{11}\\|\\\text{Si—O}\\|\\R^{11}\end{array}\right]_r\begin{array}{c}R^{11}\\|\\\text{Si—R}^{11}\\|\\R^{11}\end{array} \quad (2\text{-}1)$$

wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the Formula (2-2):

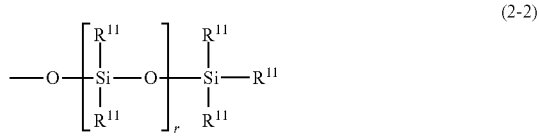

$$\text{—O}\left[\begin{array}{c}R^{11}\\|\\\text{Si—O}\\|\\R^{11}\end{array}\right]_r\begin{array}{c}R^{11}\\|\\\text{Si—R}^{11}\\|\\R^{11}\end{array} \quad (2\text{-}2)$$

wherein, $R^{11}$ and r are synonymous with those described above; and $L^1$ represents a silylalkyl group having a siloxane dendron structure expressed by Formula (3) when i=1;

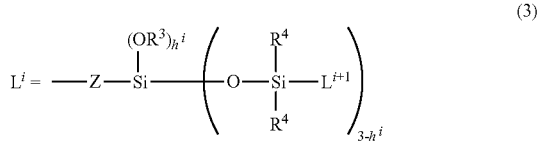

$$L^i = \text{—Z—Si}\begin{array}{c}(OR^3)_{h^i}\\|\\\\|\\\end{array}\left(\text{—O—Si}\begin{array}{c}R^4\\|\\\\|\\R^4\end{array}\text{—L}^{i+1}\right)_{3-h^i} \quad (3)$$

wherein the $R^3$ moieties are each independently a substituted or unsubstituted, straight-chain or branched monovalent hydrocarbon group having from 1 to 30 carbon atoms; the $R^4$ moieties are each independently an alkyl group or a phenyl group having from 1 to 6 carbon atoms; Z is a divalent organic group; i is a generation of a silylalkyl group represented by $L^i$ and is an integer from 1 to k when the number of generations serving as a number of repetitions of the silylalkyl group is k; $L^{i+1}$ is the silylalkyl group when i is less than k, and $R^4$ when i=k; and $h^i$ is a number in a range of 0 to 3); Q is a (poly)oxyethylene group-containing organic group; and a, b, c, and d are each numbers in the ranges of $1.0 \le a \le 2.5$, $0 \le b \le 1.5$, $0 \le c \le 1.5$, and $0.0001 \le d \le 1.5$).

7. The production method according to claim 1, wherein the organosilicon compound is obtained by reacting
(A) an organohydrogenpolysiloxane;
(B) a (poly)oxyethylene group-containing organic compound having one or more reactive unsaturated groups in each molecule; and
(C) one or more types of organic compounds selected from a group consisting of (C1) an organic compound having a number of reactive unsaturated groups greater than 1 on average in each molecule and (C2) an organic compound having one or more reactive unsaturated groups and one or more epoxy groups in each molecule (however, the use of the component (B) is optional when the component (C) contains a (poly)oxyethylene group); and the organomodified silicone is further characterized by having a silicon-bonded (poly)oxyethylene group-containing organic group and having a crosslinked structure containing a Si—C bond in a crosslinking part.

8. The production method according to claim 1, wherein the organosilicon compound is an organomodified silicone in the form of a straight-chain (poly)oxyalkylene group-containing alternating copolymer obtained by reacting at least:
(D) an organopolysiloxane having reactive functional groups at both terminals of a molecular chain; and
(E) an organic compound having two reactive functional groups capable of reacting with the reactive functional groups positioned at both of the molecular chain terminals of the organopolysiloxane (D) in the molecule.

9. The production method according to claim 1, wherein the organosilicon compound has a crosslinked structure containing a Si—O—C chain in the crosslinking part, and the (poly)oxyethylene group-containing organic block constituting the crosslinking part has at least two carbon atom bonds in the organic block and binds to a siloxane block with a chain, while the siloxane block consists of siloxane units in which 1 to 3 monovalent organic groups bind to silicon atoms, and the siloxane block has a least two silicon atom bonds.

10. The production method according to claim 1, wherein the organosilicon compound is an organomodified silane represented by Formula (8):

$$X^1_{4-(k+j)}\text{—Si}\begin{array}{c}R^{16}_j\\|\\\\|\\\end{array}\text{—Z}^1_k \quad (8)$$

wherein $R^{16}$ is a group selected from a hydrogen atom and substituted or unsubstituted, straight-chain or branched monovalent hydrocarbon groups having from 1 to 30 carbon atoms; $X^1$ is a hydrolyzable group selected from alkoxy groups, aryloxy groups, acyloxy groups, secondary amino groups, and aminoxy groups; $Z^1$ is a monovalent organic group differing from $R^{16}$ which is linked to the silicon atoms of general formula (8) by Si—C bonds; $1 \le k \le 3$; $0 \le j \le 2$; and $k+j \le 3$.

11. The production method according to claim 1, wherein the mixture further contains a solvent of the organosilicon compound.

12. The production method according to claim 1, wherein a mixture containing the organosilicon compound and the impurities is treated by an acidic aqueous solution, and water and odorizing substances produced by treatment with the acidic aqueous solution are removed by heating or depressurization.

\* \* \* \* \*